(12) United States Patent
Begleiter

(10) Patent No.: US 7,083,805 B2
(45) Date of Patent: Aug. 1, 2006

(54) EDIBLE HOLOGRAPHIC PRODUCTS, PARTICULARLY PHARMACEUTICALS AND METHODS AND APPARATUS FOR PRODUCING SAME

(75) Inventor: Eric Begleiter, Boston, MA (US)

(73) Assignee: Dimensional Foods Corporation, Boston, MA (US)

( * ) Notice: Subject to any disclaimer, the term of this patent is extended or adjusted under 35 U.S.C. 154(b) by 0 days.

(21) Appl. No.: 11/227,214

(22) Filed: Sep. 14, 2005

(65) Prior Publication Data

US 2006/0068006 A1    Mar. 30, 2006

Related U.S. Application Data

(62) Division of application No. 10/031,765, filed as application No. PCT/US00/21149 on Aug. 3, 2000.

(60) Provisional application No. 60/147,406, filed on Aug. 5, 1999.

(51) Int. Cl.
*A61K 9/20* (2006.01)
*A23G 1/00* (2006.01)
*A23G 7/16* (2006.01)
*A23L 3/015* (2006.01)
*B29C 33/40* (2006.01)

(52) U.S. Cl. ............... 424/464; 264/220; 264/221; 426/88; 426/104; 426/302; 426/305; 426/307; 426/383; 426/665

(58) Field of Classification Search ............... 424/464
See application file for complete search history.

(56) References Cited

U.S. PATENT DOCUMENTS 4,029,757 A    6/1977   Mlodozeniec et al.
4,031,200 A    6/1977   Reif
4,069,086 A    1/1978   Reif
4,668,523 A    5/1987   Begleiter (Continued)

FOREIGN PATENT DOCUMENTS

EP    0 217 821 B1 *  7/1991

(Continued)

OTHER PUBLICATIONS

Begleiter, Eric, "Edible Holography: The application of holographic techniques to food processing," SPIE, vol. 1461, "Practical Holography V" (1991).

(Continued)

*Primary Examiner*—S. Tran
(74) *Attorney, Agent, or Firm*—David G. Conlin; Peter J. Manus; Edwards Angell Palmer & Dodge LLP

(57) ABSTRACT

An edible product such as a unit dosage form of a pharmaceutically active substance includes a layer of a material that can receive and retain a high resolution microrelief that can convey information. The microrelief is themo-formable, preferably formed from an aqueous solution of HPMC and/or HPC plus a plasticizer and colorant. Other additives such as strengtheners, surfactants and adherents may be used depending on the application. The materials are selected and proportioned to control the fading or change in color of the visual image or effect produced by the relief to indicate exposure to an unacceptable degree of heat or humidity. The dosage form can be the relief-containing layer itself with the pharmaceutical carried therein. In a preferred form, the layer is an outer coating over a core containing the pharmaceutically active substance. Coated tablets are configured to resist twinning. To produce such dosage forms, the coated core is transported in unison with a flexible mold or transfer plate that can heat-replicate the microrelief on the outer layer of the dosage form, followed by a cooling and release of the transfer plate from the coating.

22 Claims, 20 Drawing Sheets

U.S. PATENT DOCUMENTS

| | | | |
|---|---|---|---|
| 4,847,090 A | | 7/1989 | Della Posta et al. |
| 4,973,469 A | | 11/1990 | Mulligan |
| 5,189,531 A | | 2/1993 | Palmer et al. |
| 5,510,171 A | | 4/1996 | Faykish |
| 5,992,742 A | * | 11/1999 | Sullivan et al. ........ 235/462.01 |
| 2004/0223156 A1 | * | 11/2004 | McGrew et al. ............ 356/364 |

FOREIGN PATENT DOCUMENTS

WO        WO9601874        1/1996

OTHER PUBLICATIONS

Article No. 15 from "Hebckoe BpeMя" No. 58 (1939) of Jan. 4, 1999 (one page).

* cited by examiner

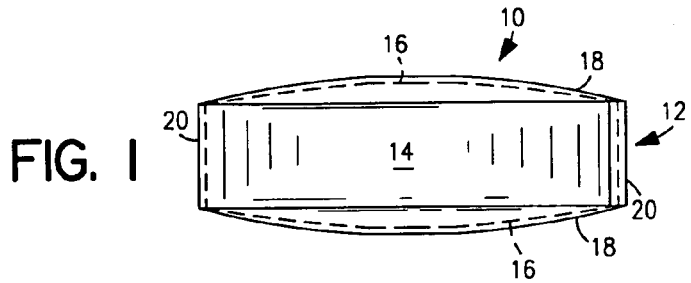
FIG. 1
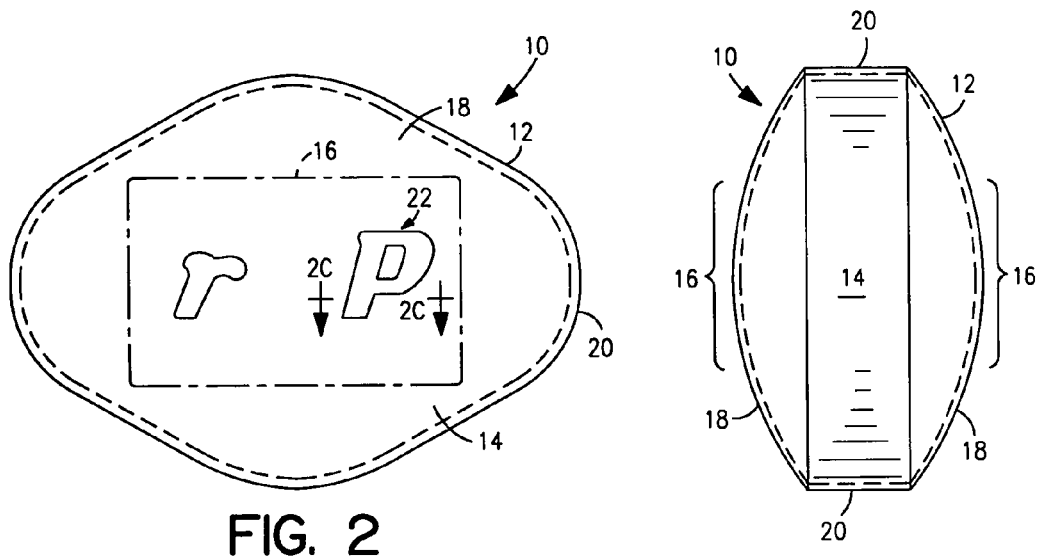
FIG. 2
FIG. 2A
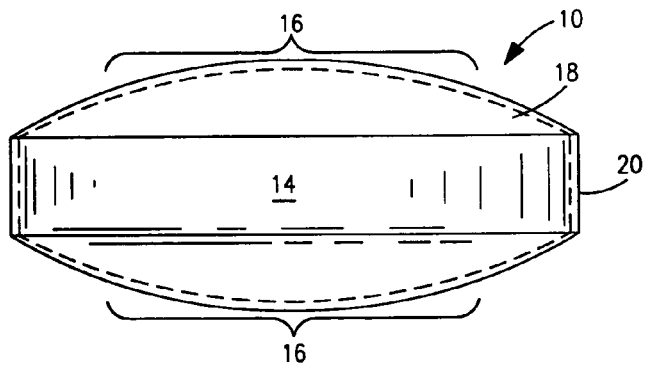
FIG. 2B
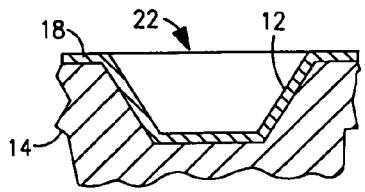
FIG. 2C

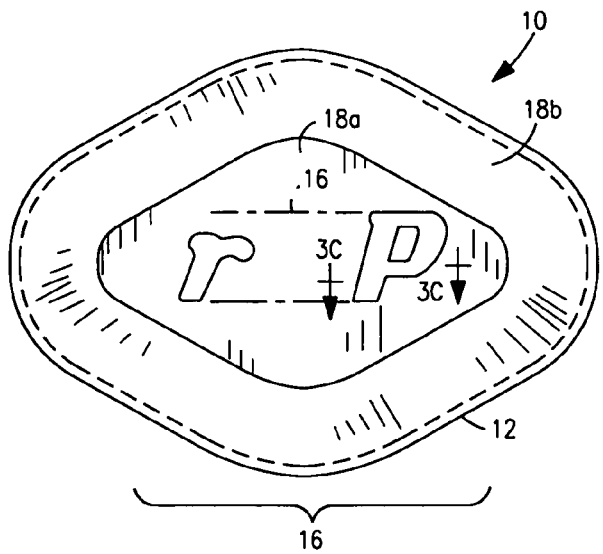
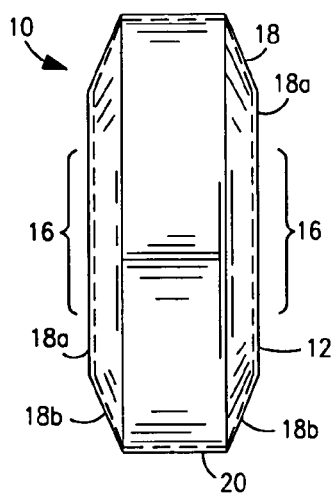
FIG. 3     FIG. 3A
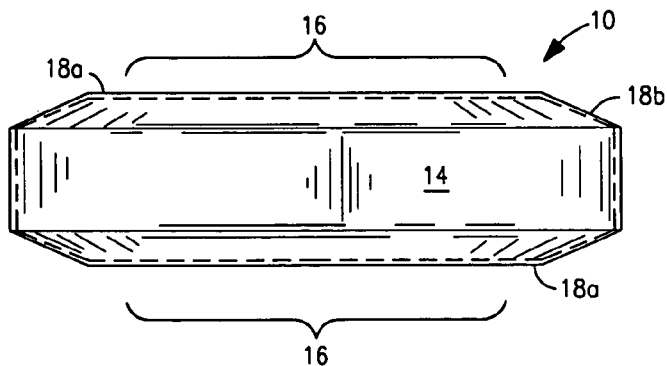
FIG. 3B
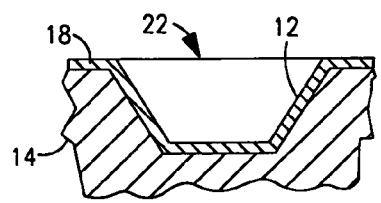
FIG. 3C

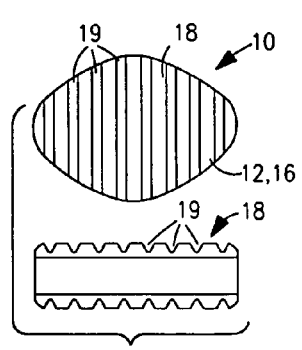
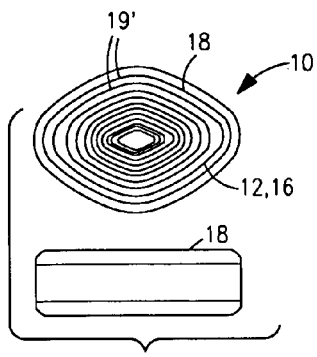
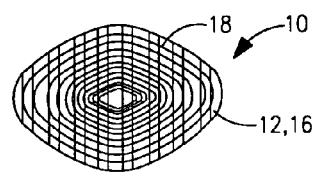
FIG. 12A  FIG. 12B  FIG. 12C
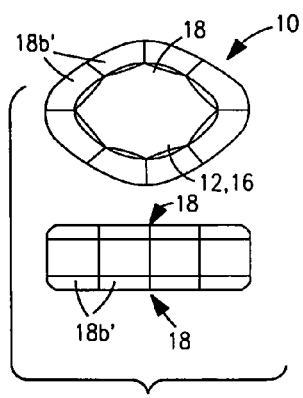
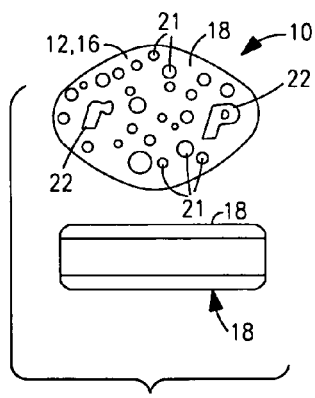
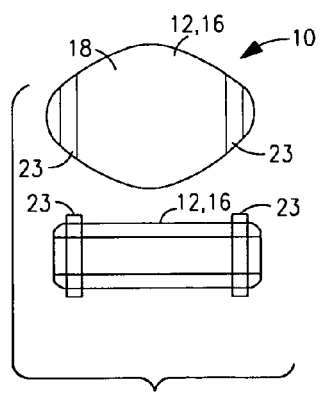
FIG. 12D  FIG. 12E  FIG. 12F
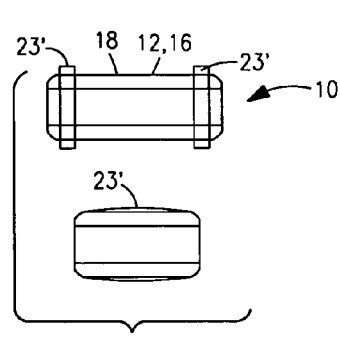
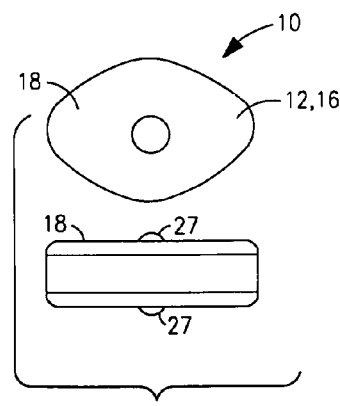
FIG. 12G  FIG. 12H

EDIBLE HOLOGRAPHIC PRODUCTS, PARTICULARLY PHARMACEUTICALS AND METHODS AND APPARATUS FOR PRODUCING SAME

CROSS-REFERENCE TO RELATED APPLICATIONS

This application is a divisional application of U.S. Ser. No. 10/031,765 filed Jan. 23, 2002, which is the U.S. national phase of PCT International Application No. PCT/US00/21149, filed Aug. 3, 2000, which in turn claims priority from U.S. provisional application Ser. No. 60/147,406 filed Aug. 5, 1999, all of which are incorporated herein by reference.

FIELD OF THE INVENTION

This invention relates in general to solid dosage forms bearing diffraction reliefs capable of conveying information, such as the reconstruction of holographic images, as well as methods and apparatus for producing same.

BACKGROUND OF THE INVENTION

The creation of holographic images using fine diffraction patterns illuminated with laser light is well known. White-light "holograms" are also well known. A common example of Benton white-light "holograms" is the creation of images on credit cards and the like to prevent tampering with information carried on the cards, and to enhance their visual aesthetics. Known images include rainbow-like color patterns, pictures, and changes in color or location of pictures or parts of pictures with a change in viewing angle.

While it is also known to emboss a suitable relief on a section of a generally flat sheet of plastic material, such as that forming a credit card, with a heated metal die, the production of high resolution diffraction reliefs on edible products presents special problems. Materials suitable for receiving and retaining diffraction reliefs on edible products must not only be capable of receiving a fine pattern, e.g., 1,000 to 5,000 lines per mm, and be capable of retaining that fine pattern (be stable), but they must also be food safe and palatable. Retention requires resistance to mechanical degradation during routine handling as well as the adverse effects of water, especially air-borne humidity and heat. Ingestibles should also be digestible, which typically means they should be water-soluble. (Pharmaceutical delivery systems are known which rely on stomach acid to dissolve a coating, or which have a substantially indigestible coating with small holes through which a pharmaceutically active substance is released.)

U.S. Pat. No. 4,668,523 to Begleiter discloses the first system for applying a high resolution diffraction gratings to a food product to produce edible holograms.

While such diffraction reliefs produced by dehydration in molds have proven to be able to provide color and other visual effects on candies and other food products, they have not heretofore been used commercially on dosage forms such as pharmaceuticals. Indeed, the commercial production of small, holographic-bearing dosage forms introduces problems, enumerated below, not encountered using the known general methods for creating holographic foods such as lollipops.

Pharmaceutical products are typically sold and used in a variety of forms, each providing a known unit dosage of a pharmaceutically active ingredient. Typical forms include common compressed powder tablets and coated tablets. The term also includes hard shell capsules and soft-gel capsules. For the purposes of this application, these and other unit dosage delivery forms are termed "dosage forms". These dosage forms typically include a core which, in turn, include a pharmaceutically active ingredient and a pharmaceutically acceptable inert carrier. In many instances, the dosage form also includes an outer layer that encloses the core, protects it, contains it (e.g., a capsule holding a granular, powdery, or viscous core material), and/or provides a vehicle for carrying a material that facilitates use of the dosage form, e.g., a "buffered" coating on an aspirin tablet.

In the pharmaceutical field, it is important to identify and differentiate one product from another reliably. The consumer needs to be sure of what medicine he/she is taking. The manufacturer is interested in establishing brand identity and extending brand loyalty. It is also of interest to be able to deter counterfeits and to covertly differentiate dosage forms, e.g., for use in double blind tests.

Pharmaceuticals and food products have been limited to the use of certain FDA and other internationally approved colors produced chemically by dyes and lakes. Many countries have different regulations governing the use of these chemicals leading to difficulty in creating uniform product identities for pharmaceutical companies across international borders. Further, it would be desirable to have the capability of producing a greater variety of colors beyond the few that have regulatory approval—especially "rainbow-like" effects produced by the juxtaposition of multiple colors of gradually varying wavelength.

Monitoring of storage conditions is important in preserving product integrity.

"Edible Holography: The application of holographic techniques to food processing", SPIE, Vol. 1461, "Practical Holography V" (1991) at pages 102–109 discusses the use of a punch die to compress a powder into a tablet while simultaneously using a metal die plate to impress a microrelief as the powder becomes a solid core in a tablet press. Rapid die wear and difficulty in releasing the compressed core from the die are just some of the problems that limit this technique.

More generally, a commercially viable system for holographically conveying information on pharmaceuticals must address a variety of requirements beyond those discussed above for food products. A major difference is that pharmaceutical dosage forms are "non-deposited", that is, they are not poured into a mold as a liquid to be formed, as with hard candy. Also pharmaceutical dosage forms are small as compared to present commercial edible products such as lollipops, and they can have non-planar outer surfaces where it would be desirable to carry a holographic diffraction pattern. In addition, the material in which the microrelief is formed cannot interact adversely with the pharmaceutically active ingredient(s) to reduce its efficacy, and should not otherwise be objectionable when ingested, e.g., allergenic. The image-producing microrelief on a dosage form must also be reliably durable and stable during manufacture, packaging, shipment, and under acceptable storage conditions, that is, conditions that do not adversely affect the efficacy or required product life of the dosage form. The microrelief should have a long shelf life, which requires a high resistance to changes in shape on the micron scale due to applied mechanical stresses, and degradation due to temperature changes or to the absorption of moisture. Such a microrelief is termed "stable". If applied as a layer on a core, the layer containing the relief should not delaminate or "bubble". Bubbling is a particular concern when heat is used in applying or processing the layer.

Suitable microreliefs used on pharmaceuticals should be compatible with modern dosage form manufacturing equipment and techniques and be economical in its implementation. A microrelief must also be non-detrimental to the efficacy of the pharmaceutical. Any heat used as part of the manufacturing process for implementing a microrelief should not degrade the efficacy of pharmaceutically active ingredient(s). While holograms transfer and reconstruct best on flat surfaces, coated tablets with flat faces tend to adhere to one another, or "twin", during the coating process. The production of diffraction microreliefs on coated products should resist twinning in order to maintain acceptable yield ratios. Suitable microreliefs should also be formed using materials that do not require new regulatory approval.

It is also desirable to know if an ingestible product is likely to have retained its efficacy after it has been manufactured and stored. Stated in other words, it would be useful to have a readily visible indicator of the environmental history of any given dosage form. Such an indicator, for example, would usefully indicate whether a dosage form had been exposed to high temperatures, e.g., over 100° F., and high humidities, e.g., over 80% relative humidity (RH), for any extended period of time during storage or prior to sale or use. This problem is commonly addressed by printing an expiration date on a container for the product. However, it would be better if there was some visual indication of efficacy on the product itself.

It is therefore a principal object of this invention to provide an edible product, including a dosage form in any of a wide variety of shapes and configurations, that has a stable microrelief whose stability can be controlled, and that conveys information such as visual holographic images and effects.

Another principal object is to provide specific, approved materials, methods and apparatus for producing such a product that are cost effective and compatible with modern high-speed production equipment and techniques such as tablet coating apparatuses.

Yet another object of this invention is to provide a system for introducing holographic brand identification for a wide range of edible products in a wide range of forms.

Another object is to provide a visual quality control indication on each dosage form in the form of a hologram that visibly changes if the dosage form has been exposed to severe adverse conditions of temperature or humidity.

A further object is to provide a system for controlling and detecting counterfeit dosage forms.

Still another object is to provide dosage forms with covert identifiers suitable for use in double blind studies.

Another object is to provide the foregoing advantages without requiring a new regulatory approval of the dosage form.

Yet another object is to provide color and visual images and effects for food products and for pharmaceuticals, (1) without the use of FDA regulated colors, dyes, inks, or metals, or (2) with colors other than those which are FDA approved, or (3) with the use of FDA approved colorant only as a contrast color to make holographic effects and images more readily visible.

SUMMARY OF THE INVENTION

Broadly stated, the invention provides pharmaceutical dosage forms and other edibles products bearing a microrelief, and in particular a high resolution diffraction relief. The diffraction relief is thermoformed in a layer of a suitable material, and once formed, is stable. The invention further provides the materials, apparatus and processes whereby such diffraction reliefs can be applied. By means of this invention, a microrelief capable of diffracting light may be applied directly to a product such as a dosage form.

The present invention allows monitoring of storage conditions to preserve product integrity. Edible diffractive gratings as a structural component of a dosage form have the ability to make visible to the unaided eye microscopic changes, caused by heat and moisture, which can alter the depth and spacing of the grating and so change the ways in which it interacts with light. Thus over-all coating changes such as expansion even as small as the wavelength of light can be detected by the unaided eye through changes in color reconstruction angles and diffraction efficiency.

The invention provides the economical production of edible colors without the necessity of adding to the product objectionable materials such as certain dyes, inks, aluminum lakes, metals such as gold or silver or minerals such as mica.

In one embodiment of this aspect, the invention provides a dosage-form comprising:

a core which comprises a pharmaceutically active substance and a pharmaceutically acceptable carrier;

a thermoformable solid outer layer overlaying said core, and a microrelief in said layer.

The layer of material that retains the microrelief in one form is pan coated onto the core and completely encloses it. In another form this layer partially covers the core. It can be printed or laminated onto the core. In still another form, the layer itself can contain a pharmaceutically active material and constitute the entire dosage form.

This layer is formed from an aqueous solution of a thermoformable material selected from the group consisting of modified cellulose, modified food starch, gelatin, waxes, vegetable gums, and combinations thereof. The preferred material comprises a modified cellulose, namely, hydroxypropylmethylcellulose (HPMC), hydroxypropylcellulose (HPC), and mixtures thereof.

The material also preferably includes a plasticizer and a colorant. The choice of plasticizer and/or thermoformable material and the relative portions are adjusted to control the response of the microrelief over time to humidity. Oils and waxes with varying melting points admixed to this layer provide control over the response of the microrelief over time to temperature. Fading or change of color (due to a change in the reconstruction angle) of the visual image or effect produced by the microrelief provides a visual indication of the environmental history of the dosage form and its integrity. Suitable waxes include paraffin (a low melting point) and carnuba (a high melting point). Suitable hygroscopic plasticizers include sugars such as dextrose (highly hygroscopic) and proplyeneglycol.

When the dosage forms are made by pan coating, the cores are configured to resist twinning by reducing the amount of the flat area at the outermost surface of the dosage form and by convexly curving the outermost surfaces, particularly the faces of tablets. Flat area reduction includes forming a recess in each face of a tablet with a generally flat-bottom that receives and retains the microrelief.

Broadly stated, a method of producing a microrelief on a dosage form according to the present invention includes the steps of:

a. coating the core with a layer of a thermoformable material that can receive and retain a holographic diffraction pattern;

b. providing a plate having a holographic diffraction pattern formed on at least a portion of a first surface thereof;

c. transporting said coated cores to a position opposite that first plate surface;

d. heating at least one of the plate and the coated layer during or prior to the time when they are in said opposed relationship;

e. pressing the first plate surface into the coated layer to replicate the holographic diffraction pattern in the coated layer;

f. cooling the coated layer thus replicated; and g. demolding the first plate surface from the coated layer.

Broadly stated, apparatus for the continuous (non-batch) production of a mircorelief on a core which can contain a pharmaceutically active substance and which is coated with a thin layer of a thermo-formable, includes a conveyor that carries the coated cores in a first direction, a plate containing a holographic diffraction pattern on one surface thereof facing the coated cores on the conveyor, the plate being movable along the first direction in coordination with the carrying, and with the one plate surface spaced from the coated cores, a heater for rapidly raising the temperature of one of the plate and the thin layer of coating to a level where the coating layer is formable, apparatus for pressing the one plate surface into the coating layer after the heating to replicate the diffraction pattern in the coating layer, a cooler to rapidly lower the temperature of the coating layer to stabilize the diffraction pattern in the coating layer, and apparatus to separate the one plate surface from the coating layer.

These and other features and objects will be readily understood from the following detailed description of the preferred embodiments that should be read in light of the accompanying drawings.

BRIEF DESCRIPTION OF THE DRAWINGS

FIG. 1 is a view in end elevation of a coated, curved-face tablet according to the present invention;

FIG. 2 is a top plan view of an alternative coated, curved-face tablet according to the present invention with lettering on one face;

FIG. 2A is a view in end elevation of the tablet shown in FIG. 2;

FIG. 2B is a view in side elevation of the tablet shown in FIGS. 2 and 2A;

FIG. 2C is a detailed view in vertical section of the lettering taken along the line 2C—2C in FIG. 2;

FIG. 3 is a top plan view corresponding to FIG. 2 of an alternative embodiment according to the present invention with flat faces and sloped edges;

FIG. 3A is a view in end elevation of the coated tablet of FIG. 3;

FIG. 3B is a view in side elevation of the tablet shown in FIG. 3;

FIG. 3C is a detailed view in vertical section of the lettering taken along the line 3C—3C in FIG. 3;

FIGS. 12A–H each show alternative arrangements in both top plan and side elevational views, except FIG. 12C which is in plan view only, according to the present invention for controlling twinning of coated tablets;

DETAILED DESCRIPTION OF THE PREFERRED EMBODIMENTS

While the present invention can be used to create reliefs in a variety of ingestible dosage forms, including confections, it is described primarily with respect to use on pharmaceutical products.

As used herein, "microrelief" means a regular pattern of grooves and ridges or the like that displays optical information or a visual effect, when exposed to suitable radiant energy. "Diffraction relief" or "grating" and "microrelief" include both (1) patterns of the grooves and ridges produced through laser light interference, with ruling engines, and with other known techniques which can be subsequently transferred to the dosage form by a mold or radiant energy and (2) visual information, images and effects produced by these patterns of grooves and ridges when properly illuminated. A true hologram records the interference pattern produced from a laser (coherent) light source with its output beam split, and the image or effect is its laser light reconstruction. As used herein, "hologram" and "holographic" are intended to include the production of optical information, images and effects on the dosage form as well as their reconstruction, using either laser light or white, incoherent light.

In a preferred embodiment, the diffraction relief is a high resolution diffraction relief. "High resolution" refers to a diffraction relief that is capable of diffracting visible light and having at least 400, and typically 1,000 to 5,000, lines per mm (a ½ to 1 micron phase displacement of grating). The dimensions of the diffraction relief are proportional to the wavelength of the light it is to interact with. The Information recorded and conveyed by the microrelief can be color, depth, image, optical data, and or a kinetic effect.

Figure 8:
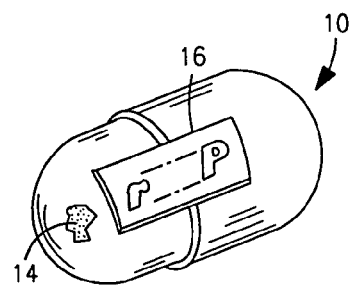
FIG. 8 is a perspective view of a capsule according to the present invention with a portion broken away to show a loose or viscous core material contained therein and where the capsule itself has a microrelief pattern formed therein.
Figure 9:
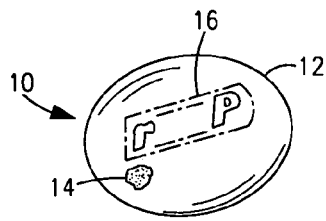
FIG. 9 is a perspective view of a soft gel capsule according to the present invention with a portion broken away to show a viscous core material contained therein and where the capsule itself has a microrelief pattern formed therein.
Figure 10:
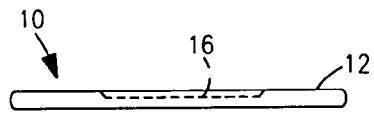
FIG. 10 is a view in side elevation of a holographic dosage form according to the present invention where a layer carrying a microrelief pattern itself has a pharmaceutically active ingredient(s) therein.

FIGS. 1–12 show various unit dosage forms 10 for the delivery of pharmaceuticals by oral ingestion. "Pharmaceutically active substance" refers to ethical pharmaceuticals as well as other orally administered, ingested products such as over-the-counter medicines. Thus, the term is used in its conventional sense to mean a pharmaceutically active compound or mixture of compounds for the treatment of a disease or condition. The term can also refer to nutritional and diet supplements which are in the form of a solid dosage form. Dosage forms utilized in the invention include all of the currently known forms such as compressed powder tablets, coated tablets (caplets), hard and soft gelatin capsules, as well as new forms such as injection-molded starch tablets, and thin-layer "sections" as shown in FIG. 10. For the purpose of this invention the dosage forms 10 which are useful within its scope will sometimes be referred to collectively simply as "dosage forms". It is understood that the dosage form core can be created with or without pharmaceutically active compounds (such as in placebos, double blind tests and confections). "Pharmaceutical dosage form" refers to a dosage form that includes a pharmaceutically active ingredient. These forms are included within the scope of the invention and can be manufactured with the disclosed methods and apparatuses. In the pharmaceutically active tablet, hard or soft gelatin capsule, and injection molded starch tablet forms, the pharmaceutically active ingredient or ingredients are typically mixed with a carrier comprising excipients that do not react with the active ingredient. A core can contain conventional pharmaceutical excipients associated with making solid dosage forms of the type previously mentioned, as well as others known to the art. Thus such excipients may, depending on the exact formula, include one or more binders, flavorings, buffers, diluents, colors, lubricants, sweetening agents, thickening agents, and glidants. Some excipients can serve multiple functions, for example as both a binder and disintegrant. Carriers and excipients are well documented in the art. See, for example *Remington's Pharmaceutical Sciences, Eighteenth Edition*, Mack Publishing Company, 1990, which is herein incorporated by reference.

The present invention creates dosage forms bearing diffraction reliefs that can convey information, visible and/or covert, to the human eye in normal (e.g., daylight and/or incandescent) and/or special (e.g., laser) illumination. In at least the preferred forms, these reliefs are formed by thermal-forming in ways compatible with current high-volume, high-speed dosage form production apparatus and methods.

One aspect of the present invention is the use of an outer layer 12 of a material that can receive a high resolution diffraction relief 16, and retain that relief pattern reliably for the intended life of the product, under anticipated conditions of manufacture, handling, storage and use. In particular, it has been found that certain materials can be: (1) formed into solid outer layers or coatings around a core, (2) subsequently heated to soften (including liquefy) the layers, (3) molded to form a high resolution diffraction relief, and then (4) cooled to retain that relief pattern in a solid form when (5) released or de-molded. General characteristics of these materials are that they have a controllable water-stability, are heat-formable, and are capable of being applied to the dosage form by known pan coating, printing, or laminating techniques. Such materials advantageously also produce coatings that are resistant to cracking, wrinkling, and/or crystallizing, can be made to flow or bond at a temperature lower than that which will adversely effect the core, can retain a grating with a phase displacement on the scale of the wave length of light, are palatable, will not interfere with the release of the cores contents, and have controllable heat and water stability in storage so as to accurately control the fading or color. This controllable changes seen as a fading or color provides a readily visible indication of the environmental history of the dosage form, and its quality.

Reference to a thermoformable "layer" 10 shall be understood to include plural thermoformable layers coated and/or deposited adjacent to each other, for example a thermoformable base coat which is colored to provide a background overlayed by a clear thermoformable layer which receives a microrelief.

More specifically, food grade materials which can function to some degree, albeit with varying degrees of stablilty, as a thermoformable outer coating to receive and retain diffraction relief include: food grade sugars (i.e., glucose, fructose, sucrose, dextrose, maltose and mixtures thereof); proteins and/or polypeptides such as albumin, casein, fibrin, and collagen and gelatins, particularly Bloom strength 150 to 250 gelatins; lipids such as oils, triglycerides, and fats; controllable melting point waxes such as paraffin, carnuba, and bees; and various polysaccharides, namely, carbohydrates such as cellulose and starches, complex gels, modified cellulose, and hydrocolloids. Suitable modified celluloses, which are presently preferred, include hydroxypropylcellulose (HPC) and hydroxypropylmethycellulose (HPMC).

For the dosage form 10 of the present invention, the diffractive relief containing layer 12 is preferably formed in two coats of (1) a color coating or layer of an aqueous solution of the modified cellulose HPC and/or HPMC, a plasticizer, and a contrast colorant to make the hologram more readily visible (2) a second clear coat of HPMC that overlies and covers the color coat. If no colorant is used, either in the core or the thermoformable layer 12, a microrelief carried in the layer 12 may not be readily visible. It can function in the nature of a watermark in quality papers. Such holograms, using no colorant in the core and a clear layer 12, can function to control counterfeits and provide the advantages of covert information.

For the holographic pharmaceutical 10 of the present invention, adherents such as a water-based shellac, and gum starches such as gum acacia, are used in some formulations, particularly where it is desired to adhere the layer 12 to a core 14 or to adhere a label of the layer 12 to a core or to an outer coating on a dosage form.

The following Table I are examples of materials which have been mixed in an aqueous solution and tried as high resolution relief-containing layers for the pharmaceuticals dosage forms 10:

TABLE I

| Modified Cellulose | Plasticizer | Colorant | Other Constituent Ingredient |
|---|---|---|---|
| 1. HPMC P5/6 | Maltodextrin DE 40 | | |
| 2. HPMC P5/6 HPC LF | | | |
| 3. HPMC 606 | | | |
| 4. HPMC E-15 | | | Shellac (adherent) |
| 5. HPMC | Triacetin | Spectraspray ™ Purple (0–340) | |
| 6. HPMC | | | monodiglyceride (surfactant) Shellac (adherent) |
| 7. HPMC 606, 100 g | | Spectraspray red D360a, 8 g | Peg 400, 14.8 g (surfactant) Water, 51.8 g |
| 8. HPMC 606, 100 g | | Spectraspray 1072, 8 g | Peg 400, 2 g (surfactant) Water, 16 g |
| 9. HPMC 600, 100 g | Triacetin, 2 g | Spectraspray 1072, 8 g | Water, 14 g |
| 10. HPMC 606, 50 g | Myracet, 2 g monodiglyceride | Spectraspray 1072, 8 g | Marcoat™ 125 Shellac, 20 g (surfactant) Aspartame 0.015 g (sweetener) |
| 11. a. Undercoat HPMC Lactose | | Titanium dioxide DF&C blue #2, aluminum lake | Lactose (flavoring) |
| b. Overcoat HPMC | Triacetin | | |
| 12. HPMC 2910 | Polyethyleneglycol 3350 | Titanium dioxide | |
| 13. a. Undercoat HPMC e-5 | Polyethyleneglycol 3350 | Titanium dioxide FD&C blue #2, aluminum lake | |
| b. Overcoat PHMC e-5 | Polyethylene glycol 3350 | | |

TABLE I-continued

| Modified Cellulose | Plasticizer | Colorant | Other Constituent Ingredient |
|---|---|---|---|
| 14. Gelating, 250 Bloom strength | | Yes | Corn syrup (strengthener) glycerin |

The HPMC grades (e.g., "P5/6") above those of its manufacturer, Dow Chemical Co.
"Spectraspray" is a trade description of a liquid colorant of Warner-Jenkins, Inc.
"Marcoat" is a trade description of an aqueous shellac solution of Emerson, Inc.
"DE 40" means "dextrose equivalency of 40%".

Examples Nos. 11 and 13 use two complete coatings; both can be applied using conventional rotating drum "pan" coaters on tablets. The undercoat preferably carries colorant; the overcoat is clear and shiny as well as highly stable on holding and maintaining a microrelief pattern. Strengtheners such as shellac, low conversion glucose syrup, and other such high molecular weight, highly cross-linked materials can be added to toughen the layer, both to retain the pattern during release from a thermal-forming die, and afterwards in handling, storage, and use. In general, long chain, high molecular weight, highly cross-linked materials add strength and stability to the microrelief carrying layer 12. Surfactants reduce the surface tension of the layer 12; they control "beading".

Colorants produce a desired background or contrast color for the dosage form and the holographic image or effect produced by the microrelief. Colorants can make the relief more readily observable.

Because the layer 12 is ingested and is taken by the mouth, the layer 12 can also include sweeteners to facilitate sucking and/or swallowing the dosage form or food product.

EXAMPLE 1

This example illustrates practicing a preferred embodiment using standard materials and coating equipment.

A first solution for applying a first (color) layer using a standard, side-vented rotating pan coater (available under the registered trademark ACCELACOTA from Thomas Engineering, Chicago, Ill.) was made by mixing the following components:

| Component | Amount, wgt % |
|---|---|
| aqueous solution containing 10% by weight HPMC | 78% |
| triacetin (plasticizer) | 1.6% |
| Black FD&C color, FD&C Blue 2 Lake, Red 40 Lake, FD&C Yellow 6 Lake | 6.4% |
| Water | 14% |

The final coating solution contained approximately 12% solids by weight.

2 kg of compressed powder tablet cores of the type shown in FIG. 3 (an arc diamond shape, 0.4020 inch wide by 0.5540 inch long and about 0.243 inch thick at its center) and described further below were coated in the aforementioned ACCELACOTA rotating pan cooling machine with a 15 inch rotating pan and operated under the operating conditions shown in Table 1, wherein the conditions designated in the Table are those commonly understood in the art.

TABLE 1

| Time Minute | Wt./ ml | Inlet Temp C. | Exhaust Temp C. | RPM | CFM | Atm. Air PSI | Spray g/min |
|---|---|---|---|---|---|---|---|
| 0 | 0 | 70 | 52.5 | 12 | 240 | 45.9 | 0 |
| 5 | 89 | 70 | 51 | 12 | 240 | 45.9 | 17.8 |
| 10 | 185 | 70 | 50.5 | 13 | 240 | 46.2 | 19.2 |
| 15 | 280 | 70 | 50.9 | 14 | 240 | 45.7 | 19 |
| 20 | 381 | 69 | 51 | 15 | 240 | 45.5 | 20.2 |
| 25 | 481 | 68 | 50.5 | 15 | 240 | 45.6 | 20 |
| 30 | 640 | 70 | 50.2 | 15 | 240 | 45.8 | 17.7 |

In Examples 1 and 2 "Wt/ml" is the accumulated weight increase during the pancoating process in the dosage forms being coated, "ml" or "millililiter" being an approximate weight measure in grams given that one ml of water weighs one gram.
Inlet and outlet Temp C. are the air inlet and outlet temperatures to and from the coater in degrees Centigrade.
"CFM" is cubic feet per minute of this air flow through the coater and "Atm Air PSI" is the air pressure in coater in pounds per square inch.
"RPM" is revolutions per minutes, the speed at which the drum of the coater rotates.
"Spray g/min" is the rate in grams per minute that the aqueous solution of the material being coated is sprayed into the drum of the coater.
"Time minute" is the elapsed during operation of the pancoating for that coating. +

After applying the first coat, a second (clear) layer was applied from a solution containing the following components, the coat being applied under the pan coater operating conditions shown in Table 2:

| Component | Amount, wgt % |
|---|---|
| aqueous solution containing 10% by wgt of HPMC | 45% |
| triacetin | 0.5% |
| water | 54.5% |

The final solution contained about 5% solids by weight.

TABLE 2

| Time Minute | Wt./ ml | Inlet Temp C. | Exhaust Temp C. | RPM | CFM | Atm. Air PSI | Spray g/min |
|---|---|---|---|---|---|---|---|
| 4 | 53 | 68 | 50.2 | 15 | 240 | 45.8 | 13.3 |
| 8.5 | 117 | 68 | 51 | 16 | 240 | 45.9 | 15.5 |

The final weight for color layer was 3%, based on the weight of the final tablet (i.e., the core coated with both layers). The final weight gain for clear layer was 0.25%, based on the weight of the final tablet.

A microrelief was thermally transferred to the tablets using an apparatus 69 and transfer plate 76 as shown and described in FIGS. 21–24 at the preferred values given in the specification, the thermoformed microrelief being applied for about 2 seconds at a pressure of about 10 Kg/tablet and at a temperature of about 125° C.

The coated tablets were stored for 3 weeks at 85° F. and 65% relative humidity (RH). After the three week period, the tablets still retained an 80–90% diffraction efficiency. Tablets stored at similar temperatures, but at 80% RH, reached the point at which the microrelief started to fade, i.e., the point at which changes in the image on effect it produced became visible and/or detectable.

EXAMPLE 2

As described in Example 1, a first color layer was formed on tablets of the type described in Example 1 by pan coating a solution containing the following components:

| Component | Amount, wgt % |
|---|---|
| aqueous solution containing 10% by weight HPMC | 68% |
| triacetin | 0.5% |
| FDA color (Blue 2 aluminum lake) | 5% |
| lactose | 1% |
| titanium dioxide | 0.6% |
| water | 24.9% |

The final solution contained approximately 12% by weight of solids.

2.2 kg of compressed tablets of the type shown in FIG. 1 (an arcuate diamond shape, 0.4020 inch wide by 0.5540 inch long and approximately 0.198 inch thick at its highest point) and described further below were coated in the same 15 inch pan coater as described in Example 1, operated as shown in Table 3.

TABLE 3

| Time Minute | Wt./ml | Inlet Temp C. | Exhaust Temp C. | RPM | CFM | Atom. Air PSI | Spray g/min |
|---|---|---|---|---|---|---|---|
| 0 | 0 | 70 | 53.2 | 11 | 240 | 44.3 | 0 |
| 5 | 102 | 70 | 50.7 | 11 | 240 | 44.3 | 20.4 |
| 10 | 201 | 70 | 50.8 | 12 | 240 | 44.5 | 19.8 |
| 17 | 335 | 69 | 50.7 | 12 | 240 | 44.8 | 20 |
| 25 | 494 | 69 | 51 | 13 | 240 | 43.1 | 19.5 |
| 33 | 650 | 68 | 52 | 13 | 240 | 44.5 | 19.8 |

After applying the first coat, a second (clear) layer was applied from a solution containing the following components, the coat being applied under the pan coater operating conditions shown in Table 4:

| Component | Amount, wgt % |
|---|---|
| aqueous HPMC (10% solution) | 42% |
| triacetin | 0.5% |
| water | 57.5% |

TABLE 4

| Time Minute | Wt./ml | Inlet Temp C. | Exhaust Temp C. | RPM | CFM | Atom. Air PSI | Spray g/min |
|---|---|---|---|---|---|---|---|
| 0 | 0 | 69 | 53.6 | 13 | 240 | 44.3 | 0 |
| 10 | 159 | 69 | 52.5 | 13 | 240 | 43.8 | 15.9 |
| 20 | 324 | 69 | 51.2 | 14 | 240 | 43.5 | 16.5 |
| 35 | 618 | 70 | 51 | 14 | 240 | 44.2 | 19.6 |

The final weight gain for the first layer (expressed as wgt %) was about 2% based on the weight of the final tablet. The final weight gain for clear layer was 1.25%, based on the weight of the final tablet.

A microrelief was thermally transferred to the tablets using an apparatus 69 and transfer plate 76 described in FIGS. 21–24 at the preferred values given in the specification, the thermoformed microrelief being appied as described in Example 1.

The coated tablets were stored for 3 weeks at 55° F. and 50% relative humidity. After the three week period, the tablets still retained an 80–90% diffraction efficiency. Tablets stored at over 100° F. faded.

In the above preferred examples the outer coating 12 comprised two complete coatings, both being applied using conventional rotating drum "pan" coaters for tablets. Colorants in the first coating produce a desired background color for the dosage form and provide contrast for the holographic image or effect produced by the microrelief. It is also possible to add color to the core before compression. Often the particle size of the aluminum lakes and titanium dioxide utilized in the first coating—if not fine enough—can interfere with the transfer process by sticking to the mold. This results in spotty, ineffective patterns. Thus, preferably, only the undercoat or the core carries a colorant; the overcoat is clear, and it is more stable.

A plasticizer in the overcoat has been found to be particularly helpful in controlling cracking. In general, a plasticizer provides flexibility to the layer 12. Plasticizers also provide a way to control the response, over time, of the layer 12 to air-borne moisture (humidity). Plasticizers such as propylene glycol, and sweeteners such as lactose, increase the effects of moisture on the layer 12 and the diffraction relief it carries. By varying the amount and type of such hygroscopic materials, one can readily vary the hygroscopic nature of the coating making it more likely to swell in humid weather. As noted above, overall hygroscopic swelling of the coating on the scale of the wavelength of light will change the relief pattern sufficiently to be visible through changes in the effect produced by the diffraction relief. Control over the response of the layer 12 to humidity can also determine the choice and proportion of the thermoformable materials. Some suitable other plasticizers which are hygroscopic include polyethyleneglycols. Plasticizers which have been found to be not as hygroscopic, include polyhydrolic alcohols, glycerin, and triacetin.

HPC is more hygroscopic than HPMC, and the two can be mixed in various proportions to vary in a corresponding manner the stability of the grating structure in response to humidity.

Oils and waxes can be used similarly but to show the effects of heat, instead of moisture, on the layer 12 and the microrelief it carries. Some suitable waxes include mixtures of low melting point paraffin, and high melting point carnuba waxes which can be added during the pan coating process to affect the melting point of the diffraction grating. One skilled in the art can readily adjust the mixtures, and thereby control the fading of the holographic relief, over time, in response to temperature.

If the layer 12 is not coated onto a core or container (e.g., a capsule), it may be formed separately as a printed section or as a laminated section. Even without a separate adherent layer, materials in the solution forming the layer 12 can be used to enhance the ability of the layer to adhere to a core, or to a capsule, or to another coating on the core. When heated, HPMC will flow into and adhere to HPMC. The same is true of HPC. The layer 12, when used as a fully-enclosing coating for a tablet, is in the approximate range of 0.25% to 7.5% of the total weight of the dosage form.

The formulations identified above can be (1) formed into solid outer layers or coatings around a core, (2) subsequently heated to soften (including liquefy) the layers, (3) molded to form a high resolution diffraction relief, and then (4) cooled to retain that relief pattern in a solid form when (5) released or de-molded. General characteristics of these materials are that they can be made to flow or bond at a temperature lower than that which will affect the core, can retain a grating with a phase displacement on the scale of the wave length of light, are palatable, will not interfere with the release of the cores contents, and have a controllable heat and water stability in storage.

These materials are also capable of retaining a fine pattern, e.g., a ½–1 micron spacing between raised portions, when exposed to the temperature and humidity variations that are normally encountered in shipment, storage and use world-wide. Materials exhibiting these qualities are termed herein "stable". It is also significant that the materials release from a mold easily, cleanly, and without damage to the microrelief when they are cooled. They are also materials that have been approved by the responsible U.S. and international regulatory agency for use in foods and pharmaceuticals.

Layers 12 formed of these materials are used to enclose the cores as in pan coating, or partially enclose a section of the core, as when they are applied using known printing or lamination techniques. If the layers themselves are formed into sections, the sections themselves can be used as dosage forms after being made to absorb therein the contents of the pharmaceutically active agent, as described below in more detail with reference to FIG. 10.

FIG. 1 illustrates a tablet form of a dosage form 10 formed according to the present invention carrying a coating 12 which fully covers a core 14. This tablet core is typically one formed by standard powder compression techniques. The layer 12 is preferably formed of the materials described above, in particular, ones including as their principal constituent a modified cellulose consisting of HPMC, HPC, or combination thereof. A microrelief 16 capable of conveying information when exposed to suitable radiant energy, typically a diffraction relief exposed to sunlight and/or a conventional artificial light, is thermally formed, by direct and indirect methods, using apparatus and techniques described below with respect to FIGS. 13–33. The microrelief is shown as being produced on both curved and flat faces 18 of the dosage form 10. The side surface 20 of the dosage form is generally straight (viewed in vertical section or side elevation) and follows the overall outline of the dosage form when viewed from the top or bottom. This outline can, of course, assume a wide variety of shapes such as circular, oval, diamond, rounded-corner arc diamond, polygonal, or many other shapes.

A particular feature of a preferred embodiment of the invention is that the faces 18 as shown in FIGS. 1–12 are characterized by 1) a shallow, convex curvature, generally along a circular arc as shown, or 2) a small flat recess. In general it is more difficult to transfer onto and then reconstruct a microrelief on a curved surface than a flat surface. Functionally, the degree of the curvature and the amount of the flat area at the outer surface of the dosage form should be such so as to resist the twinning of tablets during the coating process and allow for a good diffraction relief to be created (the pattern of ridges and grooves in the layer 12) and reconstructed (the viewed hologram). As a functional test of the appropriate degree of twinning, preferably twinning should be controlled to limit rejected twinned tablets to less than 0.5% of the total yield. As a functional test of the appropriate degree of pattern reconstruction, preferably diffraction efficiency should be not less than 80%. Increase of pan-coating rotation speed (RPM), spray rate (g/min), run time, as well as inlet and exhaust temperature and air pressure in the coater, all affect the amount of flat area and/or degree of shallowness of curvature that can be used before twinning affects limit yield. Preferred speeds rates and temperatures are described in the above examples.

FIGS. 2–2C show an alternative curved-face dosage form (coated tablet) 10 where both faces 18 are curved to resist twinning, but curved to an enhanced degree as compared with the shallow face curvature shown in FIG. 1. This tablet 10 is also fully covered with a thermoformable outer layer 12. Both curved faces terminate at a straight side wall 20. One face of the FIG. 2 embodiment includes letters formed in one convexly curved surface 18 of the dosage form. The lettering 22 is cut into the upper face 18 of the dosage form, as best seen in FIG. 2C, thereby reducing the face area subject to twinning. The microrelief can, for example, produce a diffracted rainbow-like array of colors over the surfaces 18 and around the lettering 22. On the upper surface this effect enhances and highlights the relief lettering 22, as well as providing an aesthetically distinctive and attractive appearance.

FIG. 3-3C disclose yet another embodiment of a tablet form of a dosage form 10 according to the present invention which is fully coated with a layer 12 and carries lettering 22. In this embodiment, the holographic pattern is applied only to a generally flat, central portion 18a of the upper and lower faces 18, 18 (as shown) during the thermal forming. Again, the lettering 22 is preferably depressed from the upper surface to protect it and to surround it with a holographic effect. The upper surface 18a terminates in a surrounding shoulder portion 18b that is inclined. In the embodiment shown it is generally flat in cross section and terminates in a "straight" side 20. The simultaneous provision of a flat central portion 18a facilitates the replication of a microrelief in the layer 12 because the replication occurs on a flat surface. Depression of the lettering 22 also serves to assist in controlling twinning. The microrelief 16 typically produces color, preferably a rainbow-effect, which surrounds and highlights the lettering 22.

By way of illustration, but not of limitation, in the tablet form shown in FIGS. 3–3C, with a diamond plan configuration where the dosage form 10 has a major axis length of about 0.55 inch and a minor axis width of approximately 0.40 inch, the shoulder 18b extends laterally approximately 0.13 inch and has a height of approximately 0.02 inch. The lettering 22 is cut downwardly into the face 18 approximately 0.008 inch and preferably has sloping side, as shown in FIG. 3C this slope is preferably about 37.5°.

Figure 4:
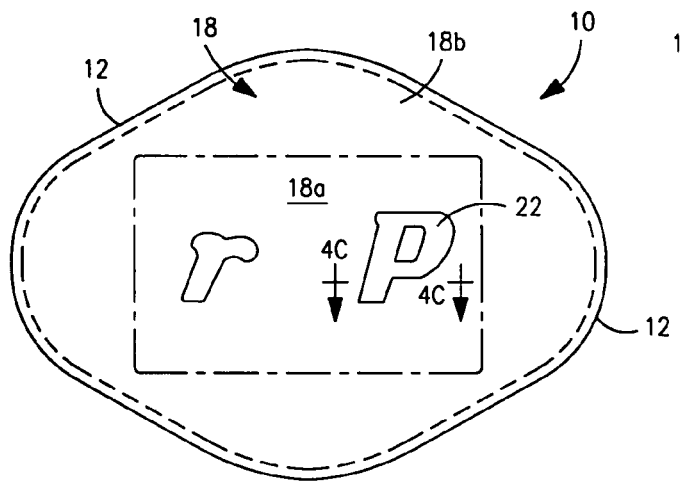
FIG. 4 is a top plan view corresponding to FIG. 3 of another coated tablet according to the present invention with flat central faces and rounded edges.
Figure 4A:
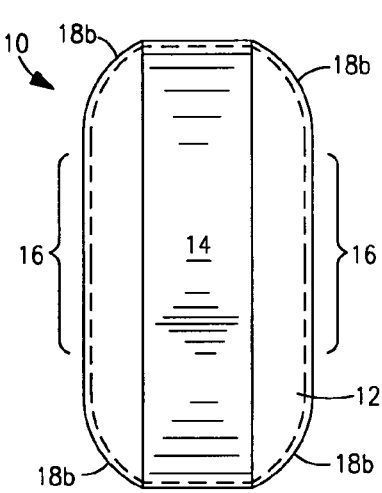
FIG. 4A is a view in end elevation of the tablet shown in FIG. 4.
Figure 4B:
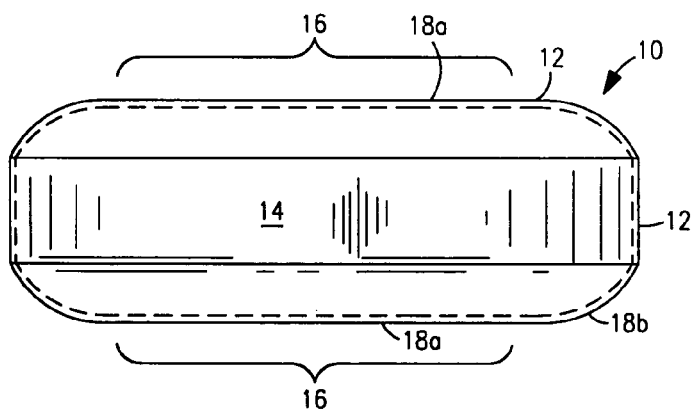
FIG. 4B is a view in side elevation of the tablet shown in FIG. 4.
Figure 4C:
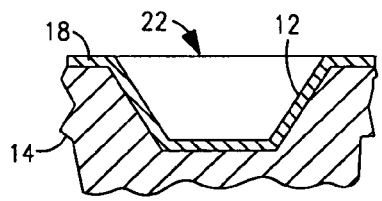
FIG. 4C is a detailed view in vertical section taken along the line 4C—4C in FIG. 4.

FIG. 4-4C show another alternative embodiment of a tablet form of a dosage form 10 according to the present invention that is fully coated with a layer 12 over a core 14. A principal difference between the FIG. 4 and FIG. 3 embodiments is that the shoulder portions 18b surrounding the flat central portion 18a are curved, preferably along a circular arc when viewed in vertical cross-section or side or end elevation. The shoulders 18b, 18b have depth, for a dosage form 10 with the illustrative shape and size described above with respect to FIGS. 3–3C, of 0.06 inch. They each extend laterally for a distance of approximately 0.10 inch. This amount of rounded shoulder embodiment has also proven to be effective in controlling twinning despite having flat face portions 18a, 18a. FIG. 4-4C represents the currently preferred form for a holographicly enhanced dosage form 10 when a dosage form is formed as a compressed pharmaceutical or sugar core enclosed in a coated layer 12 of a food grade thermally-formable material capable of receiving and retaining a fine resolution diffraction relief.

Figure 5:
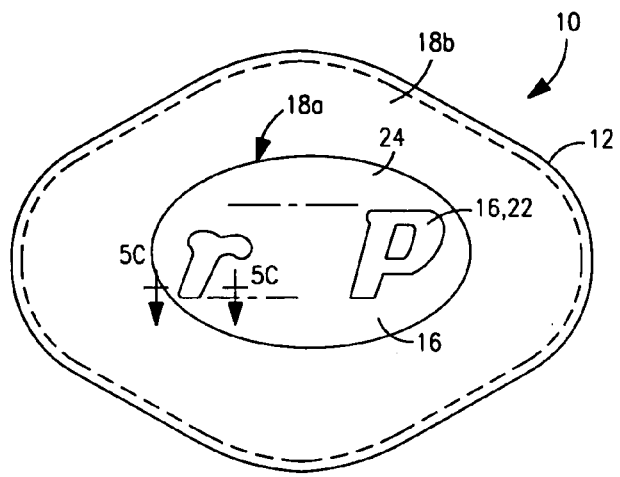
FIG. 5 is a top plan view of a flat-faced, coated tablet according to the present invention with a central recess and rounded edges.
Figure 5A:
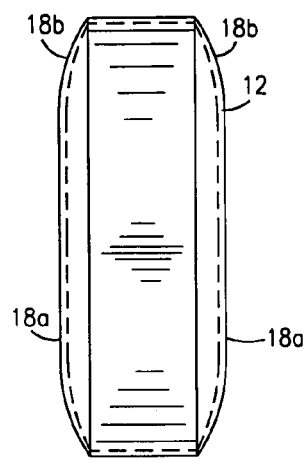
FIG. 5A is a view in end elevation of the tablet shown in FIG. 5.
Figure 5B:
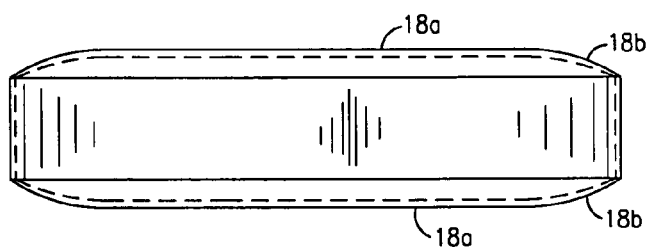
FIG. 5B is a view in side elevation of the tablet shown in FIG. 5.
Figure 5C:
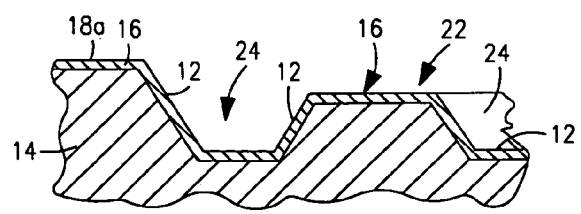
FIG. 5C is a detailed view in vertical section taken along the line 5C—5C in FIG. 5.

FIGS. 5–5C show another alternative embodiment of a tablet form of a dosage form 10 according to the present invention which is fully coated with a layer 12. Like the FIGS. 4–4C embodiment, it utilizes flat central faces 18a, 18a, and rounded shoulders 18b, 18b, but the FIG. 5-5C embodiment also has a central recess 24, 24 formed in each of the flat faces 18a, 18a. The recesses 24 each have a depth substantially equal to the height of the lettering 22 set into the recess. As with the other preceding embodiments, the configuration and dimensions can vary depending on factors such as the overall dosage form configuration and size, the nature and extent of the coating 12, and the presence of the other twinning control mechanisms. The depth of the recess into which the microrelief is transferred also helps to protect it from abrasion. In a tablet with an overall arc diamond shape as shown in FIG. 5, and with the dosage form having a major axis length of about 0.55 inch and a minor axis width of approximately 0.40 inch, the curved shoulder extends over a depth of 0.028 inch and extends laterally for approximately 0.07 inch with a curvature subtending on angle of about 0.1 radian, and the central recess 24 has a depth of approximately 0.0064 inch. The upper surface of the lettering 22 is generally co-planar with the flat surface of the surrounding face portion 18a. As shown, only the upper recess 24 contains the lettering 22. The microrelief 16 is stamped into the generally flat and co-planar portions of the lettering 22 and the surrounding regions of the flat face portion 18a.

Figure 6:
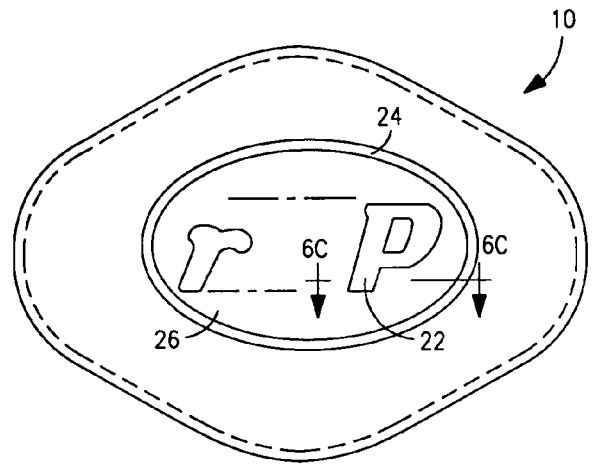
FIG. 6 is a top plan view of an alternative embodiment of a flat-faced, coated table with a double recess according to the present invention.
Figure 6A:
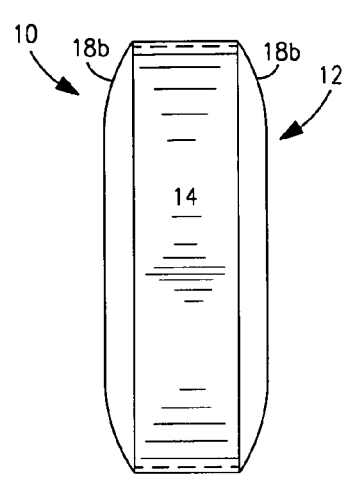
FIG. 6A is a view in end elevation of the tablet shown in FIG. 6.
Figure 6B:
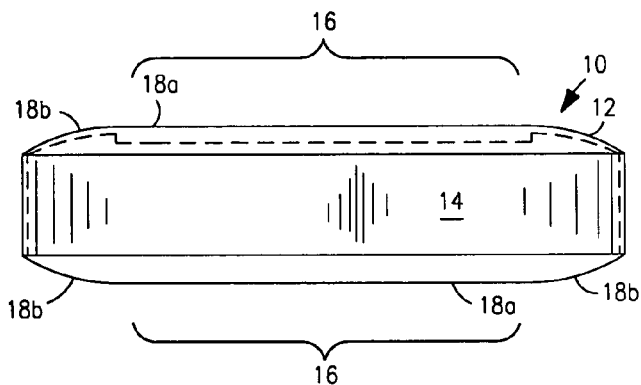
FIG. 6B is a view in side elevation of the tablet shown in FIG. 6.
Figure 6C:
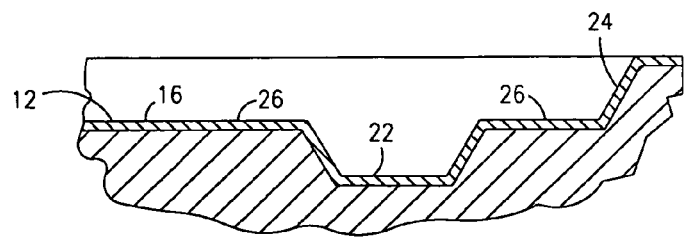
FIG. 6C is a view in vertical section taken along the line 6C—6C in FIG. 6.

FIGS. 6–6C show yet another embodiment for a dosage form 10 in the form of a tablet with a core 14 coated with a layer 12 and having rounded shoulders 18b and a central recess 24 to control twinning, all according to the present invention. The FIGS. 6–6C embodiments differ from the FIG. 5-5C embodiment principally in that the lettering 22 projects down rather than up in the central recess 26. FIG. 6C is a detailed sectional view taken along line C—C in FIG. 6 to illustrate the configuration of the recesses and the relative heights thereof. A microrelief 16 is typically formed in the layer 12 covering section 24. It may also be thermoformed in the surrounding bottom surface as well as the flat surface 18a surrounding both recesses 24 and 26. While the double recess dosage form configuration is more complex, it has the advantage of providing a flat surface 26 to receive a diffraction relief 16, while at the same time accenting the area around lettering 22. For purposes of illustration only, the dosage form shown in FIGS. 6–6C, with the same general configuration and dimensions as the dosage forms shown in FIGS. 4 and 5, has a maximum depth in the first recess 24 of approximately 0.0054 inch, and a maximum depth of the second recess of approximately 0.0064 inch. As before the depth of the recess into which the microrelief is transferred also helps to protect it from abrasion. Again, these values are merely illustrative, and in no way should be construed as limiting the scope of this invention to that particular value, or even a near range of values.

Figure 7:
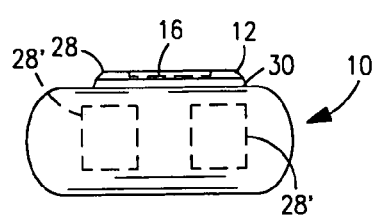
FIG. 7 is a view in side elevation of a tablet according to the present invention with a section of a layer containing a microrelief pattern, and adhered to a tablet core.

FIG. 7 shows a tablet in which a section has been applied through lamination. A compressed core 14 carrying a section 28 of layer 12, e.g., 1 to 2 microns thick, which has a high resolution diffraction relief 16 formed on its outer surface. An adherent layer 30 bonds section 28 to the outer surface of the core. The thickness of layers 12 and 30 are highly exaggerated in FIG. 7 for clarity. Suitable adherents are water and/or alcohol-soluble and non-reactive with the materials forming the core or the layer 12. They are preferably heat-activated and reliably secure the core to the section 28. A suitable adherent is wax or vegetable gum. In practice, it has been found however that the adherent will extrude or "squeeze out" along the edges of the section when it is affixed to the dosage form. To avoid this problem, the presently preferred arrangement (shown in FIG. 7 as an alternative arrangement) of adhering section 28' carrying a relief to a dosage form is to form the outer layer 12 of the dosage form and the section 28' of a material that will fuse to itself when heated. It is preferred to form the section 28' and to coat the dosage form core 14 or encapsulate the core material 14 in the same material, HPMC. Alternatively, the section applied does not have to have a preformed microrelief and so the degree of heating used to form the relief will cause the materials of section 28' and this coating or capsule to flow into one another to adhere them. This allows a smaller amount of coating to be applied during panning and so further reduce twinning. HPMC will also form a shiny surface when heat stamped which is attractive independent of a diffraction relief.

Section 28 can be applied in a continuous high-speed operation using a layer 12 in the form of a ribbon. The layer 12 is then advanced in coordination with a movement of cores 14 that place the adhesive coating 30 of each section 28 in contact with an associated core 14. They are heated when the core and sections are in an opposed relationship and in contact with one another. The heating promotes the adherence of the section to the core, and can also thermoform the microrelief pattern in the layer 12 if this replication has not occurred earlier. The adhered sections are then cooled, and the section 28 is transferred. The edible layer 12 can be a combination of HPMC, HPC and modified starch. An edible adhesive coating 30 (if a direct thermal bond is not utilized) can be a combination of waxes and vegetable gum plus triglycerides and a solvent. The transfer can be controlled and localized by using a stamper or thermal printer to transfer the section in a predetermined letter or shape by pressing against the dosage form.

As stated above, in order to address twinning issues on tablets with flat areas it is also possible to apply a section of outer coating layer 12 by lamination or printing. When printing, layer 12 is applied in a traditional tablet marking machine. The layer can be applied as a continuous section or in the form of ground solid particles of material forming the layer 12, as described above. As well as printing sections of layer 12 onto the core, machines of this type can also be used to augment layer 12 before and/or after the transfer of diffractive reliefs to accent areas and print letters to be used with the diffractive images. When printing complex images, each printed layer can be created from a different composition of layer 12, as is described in other areas of this application, so to retain the images and effects produced by its grating at different temperatures and humidity conditions. Thus complex patterns can be created which record the effects of maximum storage conditions over a range of environmental factors (i.e., ranges of temperature and humidity). By way of example, two stripes (like sections 28' described above) of layer 12 can be applied, each of which changes its image at different relative humidities. The stripes can be printed onto the dosage form, one using a layer 12 formed using the materials of Example 1 herein and the other using the materials described above with reference to Example 2.

FIG. 8 shows a hard capsule 10 that carries a core 14 within the capsule as a powdery, granular or viscous mass. The capsule shell contains and protects the core material, but in accordance with the present invention, it is also formed of a heat-formable layer 12 that can be thermal-formed with a microrelief pattern 16 directly into the inner or outer surface of the capsule. Suitable materials for the formation of the capsule include gelatin, starch, and HPMC, or mixtures therof.

FIG. 9 illustrates a soft gel capsule 10 according to the present invention which is similar in function to the hard capsule described with respect to FIG. 8, The hard and soft capsules are preferably formed of a gelatin material, preferably with a Bloom strength of 200 to 250, according to the present invention.

FIG. 10 shows a unit dosage form 10 according to the present invention where the layers themselves are formed into sections, and are used as dosage forms themselves after being made to absorb or are formed with, the contents of the pharmaceutically active agent therein. Typically layer 12 absorbs the pharmaceutical in the manner of ink blotter carrying absorbed ink, or is formed with it from a common aqueous solution. Absorption, e.g., by spraying the pharmaceutical into the pre-formed layer 12, is presently preferred. Preferred materials for this section type dosage form are HPMC, gelatins, dextrins, and vegetable gums such as gum acacia, pollulan gum, and mixtures thereof.

Figure 11:
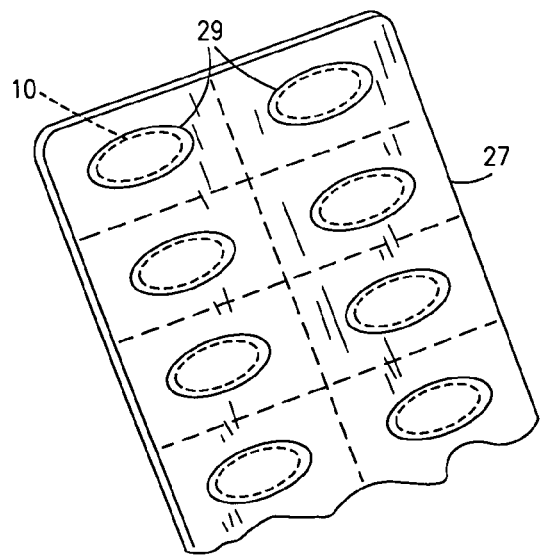
FIG. 11 is a perspective view of a package of plural dosage forms.

FIG. 11 shows a temperature and humidity controlled container for multiple dosage forms 10. It contains sections for storage 29 and a backing layer 27 which can include a thermal and hygroscopic humidity barrier to further control the moisture and temperature the dosage form 10 is made to interact with.

FIGS. 12A–H each show, in top plan and side elevation, a tablet-type dosage form 10 that is coated with a outer layer 12 that carries a microrelief 16. The tablets 10 each have an overall arcuate diamond shape in plan view and have two generally flat faces 18, 18. They differ from one another in the mechanism used to reduce the area of the faces 18, 18 to control twinning during the application of the coating layer 12.

FIG. 12A illustrates a series of lateral grooves 19 formed in the core 14 of the tablet. The area of the faces 18, 18 is reduced by the area of the grooves 19 at the faces 18, 18. The width of the grooves can be varied especially for a given tablet configuration and coating operation. The reject rate due to the twinning is the test that measures whether the groove is properly configured.

FIG. 12B shows the same tablet 10, but with a series of concentric grooves 19'.

FIG. 12C shows a tablet 10 using a combination of the grooves 19 and 19'.

FIG. 12D shows a tablet 10 with a coating 12 with two central, generally flat faces 18, 18 surrounded by an eight-sided, diamond-like array of flat-faced, inclined, shoulder portions 18b'.

FIG. 12E shows a tablet 10 with a coating 12 carrying lettering 22 cut into at least one face 18 together with a set of depressions 21 also formed in the otherwise generally flat faces 18, 18. Twinning is reduced in proportion to the combined surface area (at face 18) of the lettering 22 and the depressions 21.

FIG. 12F shows a tablet 10 with a coating 12 that has raised, enlarged portions 23, 23 at both ends of the tablet. The end portions 23, 23 control twinning by physically interfering with a face 18 to face 18 contact between tablets 10.

FIG. 12G is a variant on the FIG. 12F embodiment when the raised end portion 23' smoothly merges with the body of the tablet at both ends to reinforce the portions 23', 23'.

FIG. 12H shows another embodiment of the tablet 10 with generally flat faces 18, 18 and a central, generally hemi-spherical, projection 27 generally centered on each face 18. The projection 27 can, of course, take a variety of shapes and can be used in plural form on each face.

Figure 13:
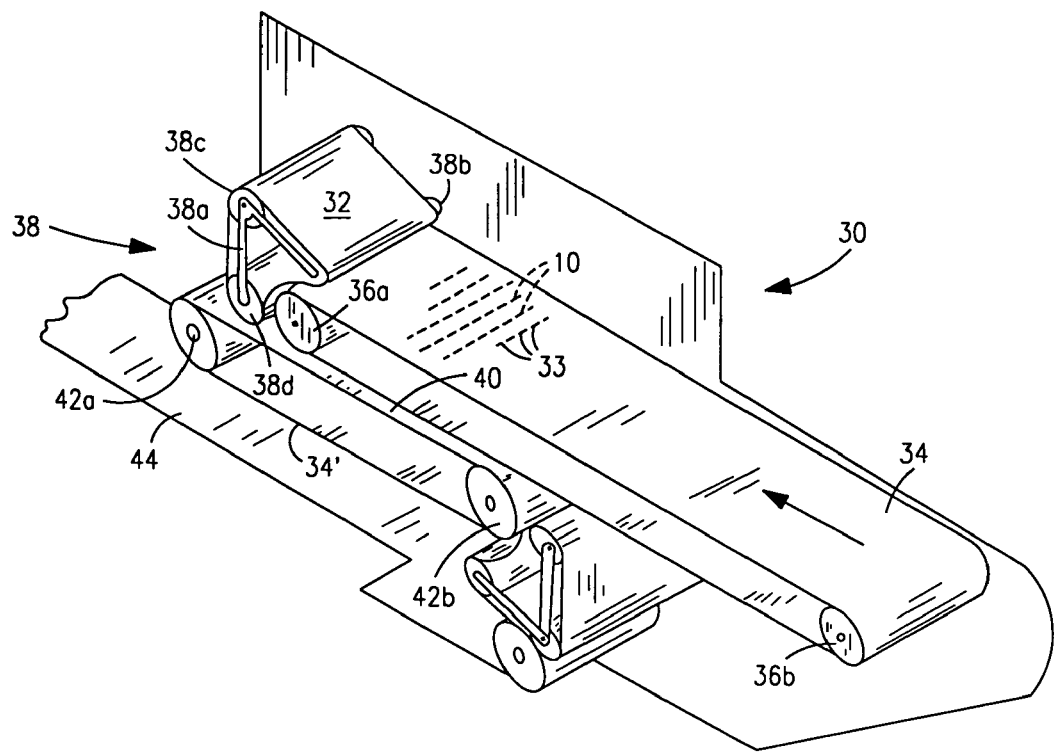
FIG. 13 is a simplified view in perspective of a belt-type apparatus according to the present invention with a moving transfer plate for manufacturing holographic pharmaceuticals also according to the present invention.
Figure 14:
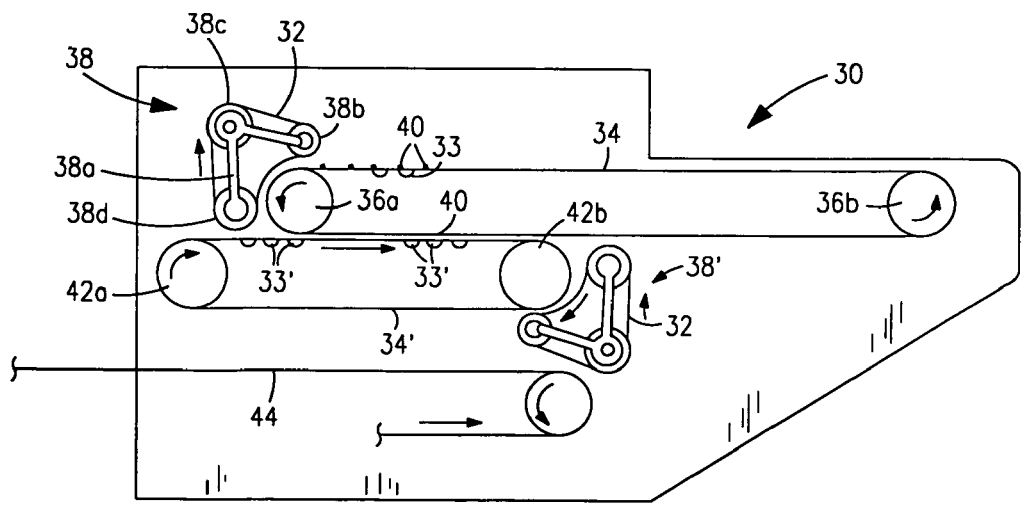
FIG. 14 is a view in side elevation of the apparatus shown in FIG. 13.
Figure 15:
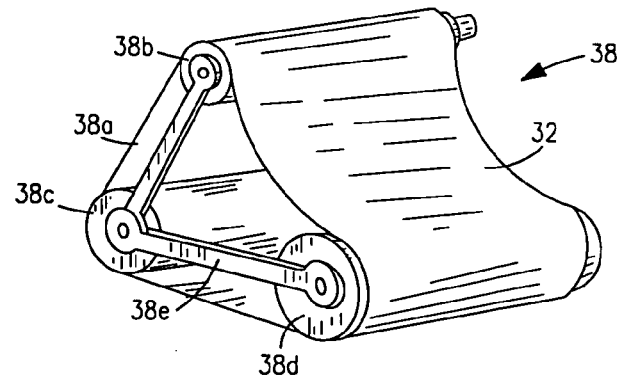
FIG. 15 is a detailed view in perspective of the moving transfer plate thermoforming assembly shown in FIGS. 13 and 14.

Turning now to apparatus and techniques and modes of processing suitable for producing the dosage forms 10, FIGS. 13–15 illustrate an apparatus 30 which uses a semi-elastic mold, or "transfer plate" 32 configured as a belt and adapted to move in coordination with an array of the dosage forms 10 each carried in suitable aligned depressions 33 on a conveyor belt 34.

As shown, the dosage forms 10, have been coated, at least in part, with a layer 12 and are arrayed across the conveying belt 34 in a series of mutually-spaced lines. A like pattern of the depressions 33 each receives one of the tablet or capsule types of the dosage forms 10 to establish this array. One of the rolls 36a, 36b that carry the belt 34 is driven to advance the dosage forms, right to left as shown, to a first relief replicating assembly 38 having a frame 38a, and three rolls 38b, 38c and 38d journalled in the frame. The rolls carry the continuous belt transfer plate 32. At least one of these rolls is also driven to move the transfer plate in coordination with movement of the belt 34.

The transfer plate 32 is preferably formed as a thin, temperature resistant sheet of a material that can retain a high resolution microrelief such as a diffraction pattern on its outer surface, which is preferably thermally conductive and able to flex sufficiently to transfer the relief to a heat-softened and/or liquefied layer 12 on one face 18 (FIGS. 1–12H) of dosage form 10 while accommodating to its shape. The preferred material is a diffractive surface composed of an electroformed metal or a heat resistant plastic, both with a thickness in the range of 1 to 5 mils. The tension in the transfer plate 32 produces a downward pressure urging the microrelief pattern on the transfer plate to be replicated in the layer 12 on the dosage forms as they pass through a nip defined by the belt 34 (at the roll 36a) and the opposed portion of the transfer plate 32.

The coating 12 is heated, preferably just before and/or during this replication, to a degree that softens it sufficiently to receive the microrelief. A typical temperature of the layer 12 produced by this heating is in the range of 90° C. to 150° C., and preferably about 125° C. It can be effected by heating the transfer plate, the dosage form coating 12, or both. The heat source can be a stream of hot air, an electric resistance heater, a pulse of a laser, a source of infra-red radiant energy, a fluid-heated cylinder, or any of a wide variety of known devices. In the apparatus shown, preferably the roll 38b is heated, and it in turn heats the transfer plate. If the dosage form is heated, it can be heated as a whole, or heated with a controlled burst of radiant energy (e.g., laser light) that heats only the outer layer 12, but does not significantly increase the temperature of the core 14. The transfer of the relief can occur in a fraction of a second, with 0.3 to 3 second being typical, and with a pressure of between 5 and 10 kg per pill. After transferring the microrelief to the layer 12, the layer is rapidly cooled to set the microrelief in the layer. Where release is a significant concern, a sliding mechanism is employed to shift the belt that holds the dosage form array to the side effecting the release. Again, a wide variety of cooling techniques can be used such as jets of chilled air, cold rolls, ambient air and radiant cooling, or the action of the cool core 14 (FIGS. 1–12H) as a heat sink. In the apparatus shown, preferably roll 38d and 36a are cooled, which cools the transfer plate 32, and the dosage forms carried on the belt 34. The cooling also aids the release of the outer layer 12 from the transfer plate.

Figure 20:
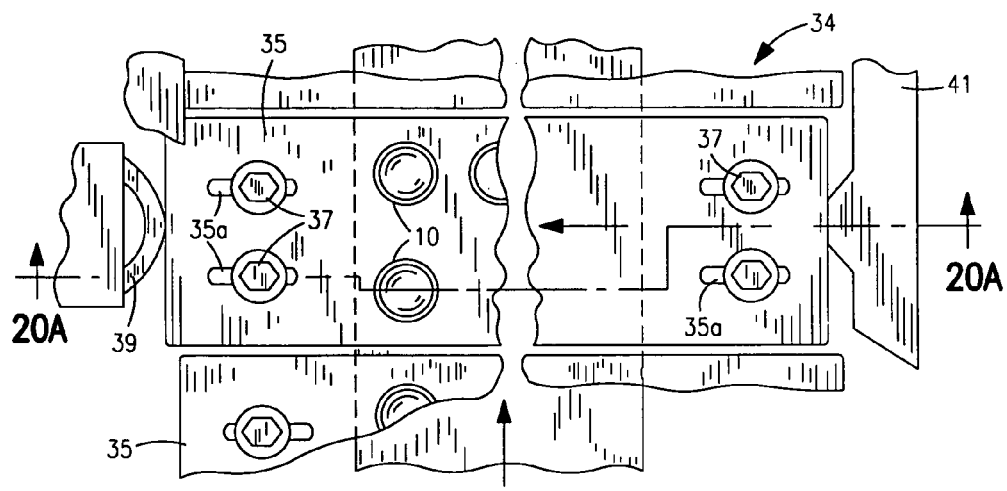
FIG. 20 is a top plan view of a slat-segment conveyor belt according to the present invention.
Figure 20A:
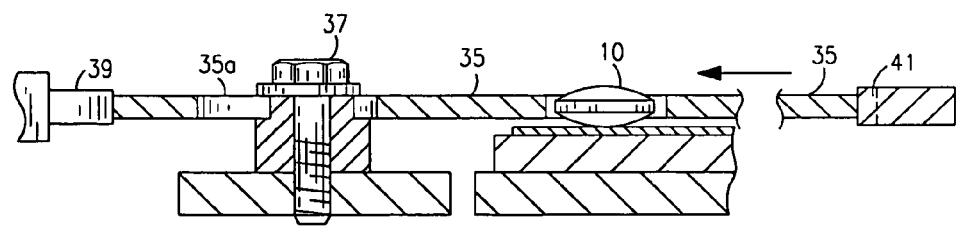
FIG. 20A is a view in section taken along the line 20A—20A in FIG. 20.

The belt 34 and transfer plate 32 move in coordination until the cooling has set the microrelief. A guide member 40 retains the dosage forms in the belt 34 as it rotates around a cushioned roll 36a to allow for variations in dosage form thickness and to invert the dosage forms 10 just embossed. While a continuous belt is shown, other conveyance arrangements can be used, e.g., a chain drive carrying a series of mutually spaced, slat-like segments 35 (FIGS. 20 and 20A) that carry the dosage forms and transfer plate. Each slat segment 35 can then be jogged along its length independently of the movement of the other segments to facilitate the release of the dosage forms from the transfer plate. The slates are preferably mounted on bolts or pins 37 captured in elongated openings 35a that guide the jogging movements. Springs 39 hold the slats in a normal position. A fixed cam plate 41 at the side of the belt 34 engages the slats as they travel and produces the jogging movement in opposition to the spring force.

The dosage forms 10 transfer to an array of depressions 33' in belt 34'. It carries them to a second print assembly 38' that transfers a diffraction microrelief on the opposite face of each dosage form 10. The assembly 38' has the same construction as the assembly 38. The microrelief pattern, of course, may differ. The presenting coated dosage form face or surfaces are heated, the microrelief pattern thermally transferred, cooled, and released, as with the assembly 38, as they are continuously carried through the assembly 38'. Upon leaving the assembly 38', the dosage forms 10 travel in belt 34' and fall onto a take-away conveyor 44.

Figure 16:
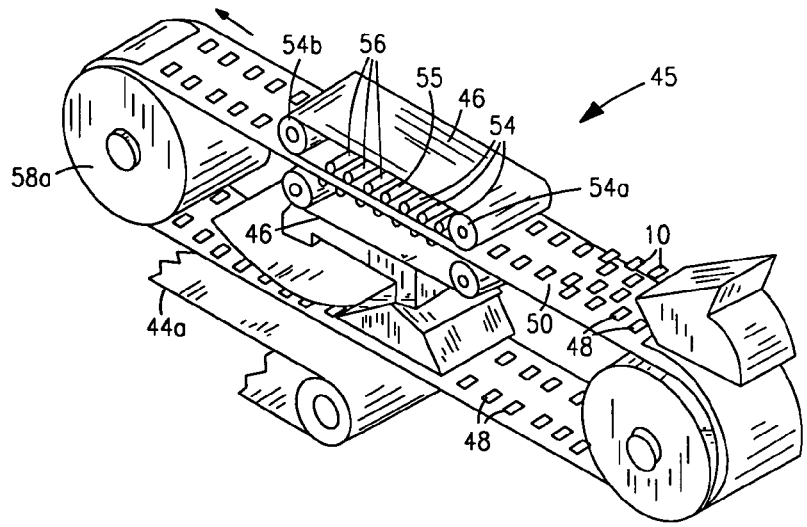
FIG. 16 is a simplified perspective view of a belt-type, twin moving transfer plate apparatus according to the present invention for manufacturing holographic pharmaceuticals also according to the present invention.
Figure 17:
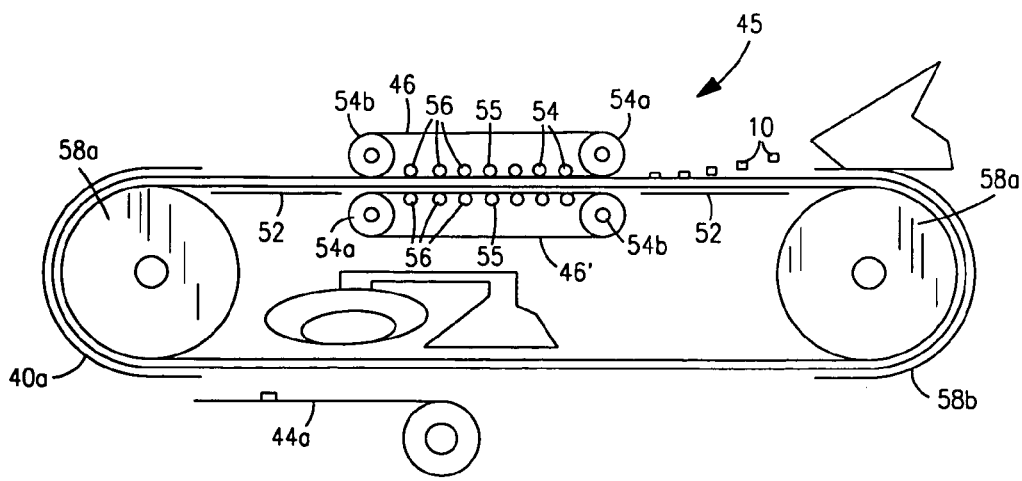
FIG. 17 is a view in side elevation of the apparatus shown in FIG. 16.

FIGS. 16 and 17 show an alternative apparatus 45 according to the present invention which, like the apparatus 30 of FIGS. 13–15, uses two transfer plates 46, 46' to replicate a high resolution diffraction relief on opposite faces 18 of dosage forms 10 carried in opening 48 of moving conveyor belt 50. The upper rim of belts 50 moves right to left, as shown, as dosage forms 10 are fed into the openings 48 which aligns and transports the dosage forms. The openings 48 extend through the belt 50. A panel 52—or a belt or other equivalent member—supports the dosage forms at their bottom to retain them in the openings 48 before and after the transfer plates 46, 46'. The transfer plates 46, 46' are each journalled on rolls 54a, 54b that drive the transfer plates in coordination with the movement of the belt 50. The transfer plates sandwich the dosage forms there between. Rolls 55 disposed behind each transfer plate adjacent the dosage forms are heated to heat the dosage forms through the transfer plates to a suitable temperature, again, preferably 90° C. to 150° C. Cooling rollers 56 then help in demolding. Note that the thinness of the transfer plates not only facilitates rapid heat transfer, but also facilitates the application of a generally uniform pressure over the dosage form surface receiving the microrelief, despite the fact that the surface might not be flat, e.g., the curved surfaces 18 of the dosage forms 10 shown in FIGS. 1–2. A uniform distribution of the pressure can be promoted by using a resilient pressure member, e.g., a foam sleeve on alternating rolls 54 and 54', and 56 and 56' below the dosage form such that each heating or cooling roller is pressing the bottom or top of the dosage form against an opposing resilient pressure member.

The transfer plates 46 and 46' can be pre-curved at the point of contact with the dosage forms to facilitate the transfer on to irregularly shaped sections. The microrelief pattern on the transfer plate can also be optically predistorted to accommodate for the reconstitution of an image on dosage forms with curved irregularly shaped sections. The dosage forms are thus simultaneously and continuously replicated with a microrelief pattern on both sides of complexly shaped surfaces and are carried around roll 58a and held in the holes 48 by a conforming guide member 40a. As the dosage forms clear the guide, they fall onto a take away conveyor 44a.

Figure 18:
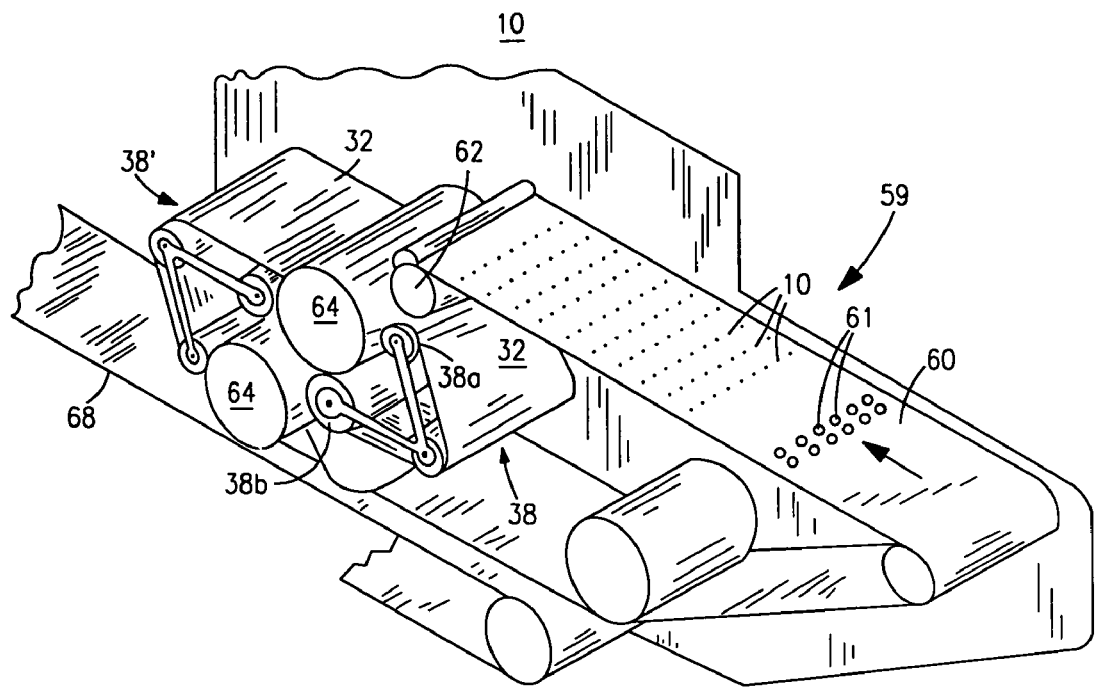
FIG. 18 is a simplified perspective view of an alternative embodiment of a belt-type, twin moving transfer plate apparatus according to the present invention for manufacturing holographic pharmaceuticals.
Figure 19:
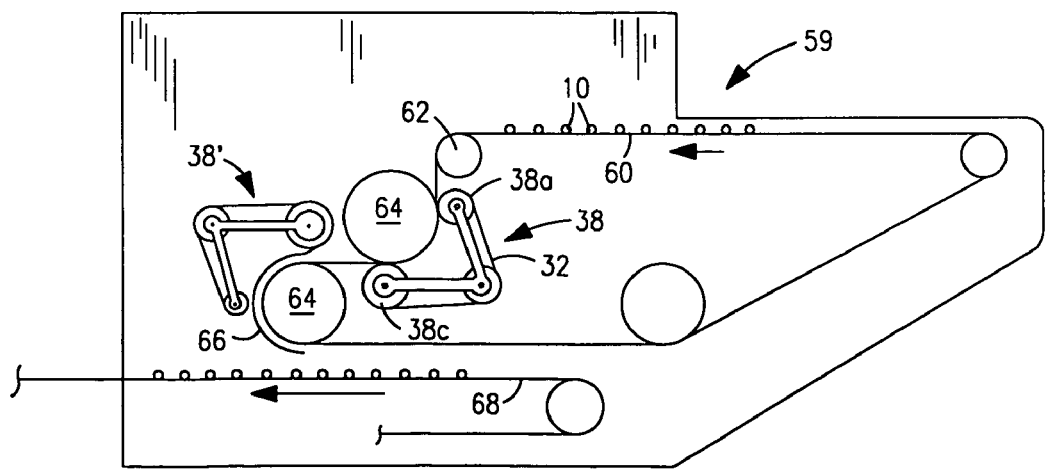
FIG. 19 is a view in side elevation of the apparatus shown in FIG. 18.

FIGS. 18–19 show a twin moving belt-like transfer plate apparatus 59 according to the present invention, which is an alternative embodiment employing features of the FIGS. 13–15 and FIGS. 16–17 apparatus 30 and 45 but which avoids the dosage form transfer between belts attendant the FIGS. 13–15 embodiments. An array of dosage forms 10 with coatings 12 on at least some portions of their upper and lower faces are transported in openings 61 formed in a continuous belt 60. The openings 61 extend through the belt 60, which acts both as a transport and an alignment grid. Its upper run travels right to left, as shown in FIG. 18, over a first roll 62 and then between a replicating assembly 38 and a backing roll 64. The first roll 38a of the assembly 38 heats the transfer plate 32 containing the microrelief pattern to be transferred, here a diffraction relief with a holographic image, which then is pressed into a layer 12 to replicate the structure. The belt tension and nip dimensions set the pressure. Preferably the backer roll and/or the transfer plate have a resilient layer that distributes the applied force generally uniformly, and urges the thin transfer plate into the layer 12 even if it is in recessed or curved portion of the dosage form. Roll 38b of the assembly 38 is cooled to set the microrelief. De-molding is as with the previously discussed embodiments.

Continued transport then carries the dosage forms through a mirror-image print assembly 38' and cooperating backing roll 64 that replicates a relief on the opposite face of the dosage forms 10. A guide 66 carries the dosage forms around to a take-away conveyor 68.

FIGS. 21–24 show another apparatus 69 according to the present invention for transferring a microrelief pattern into the coating 12 of a dosage form 10. This embodiment uses a pallet assembly 71 that has a rectangular frame 70 that supports a registration plate, or grid, 72 that in turn holds an array of the dosage forms 10 in openings 74 that extend through the grid. A thin, rectangular transfer plate 76, preferably formed of metal, and having a microrelief pattern etched or otherwise formed on one face is placed in the frame. The transfer plate 76 is registered on pins or surfaces (e.g., the interior surfaces of the sidewalls of the frame 70) if it is desired to have precise registration between the relief pattern and the dosage forms. An elastic base 77 also held in the frame 70 supports the dosage forms from the bottom. It can have depressions aligned with the openings to accommodate curved or thick dosage forms and to protect the supported surface from mechanical abrasion. The apparatus carries the pallet 71 along a generally linear processing path that includes intermittent stops at a series of stations.

Figure 21:
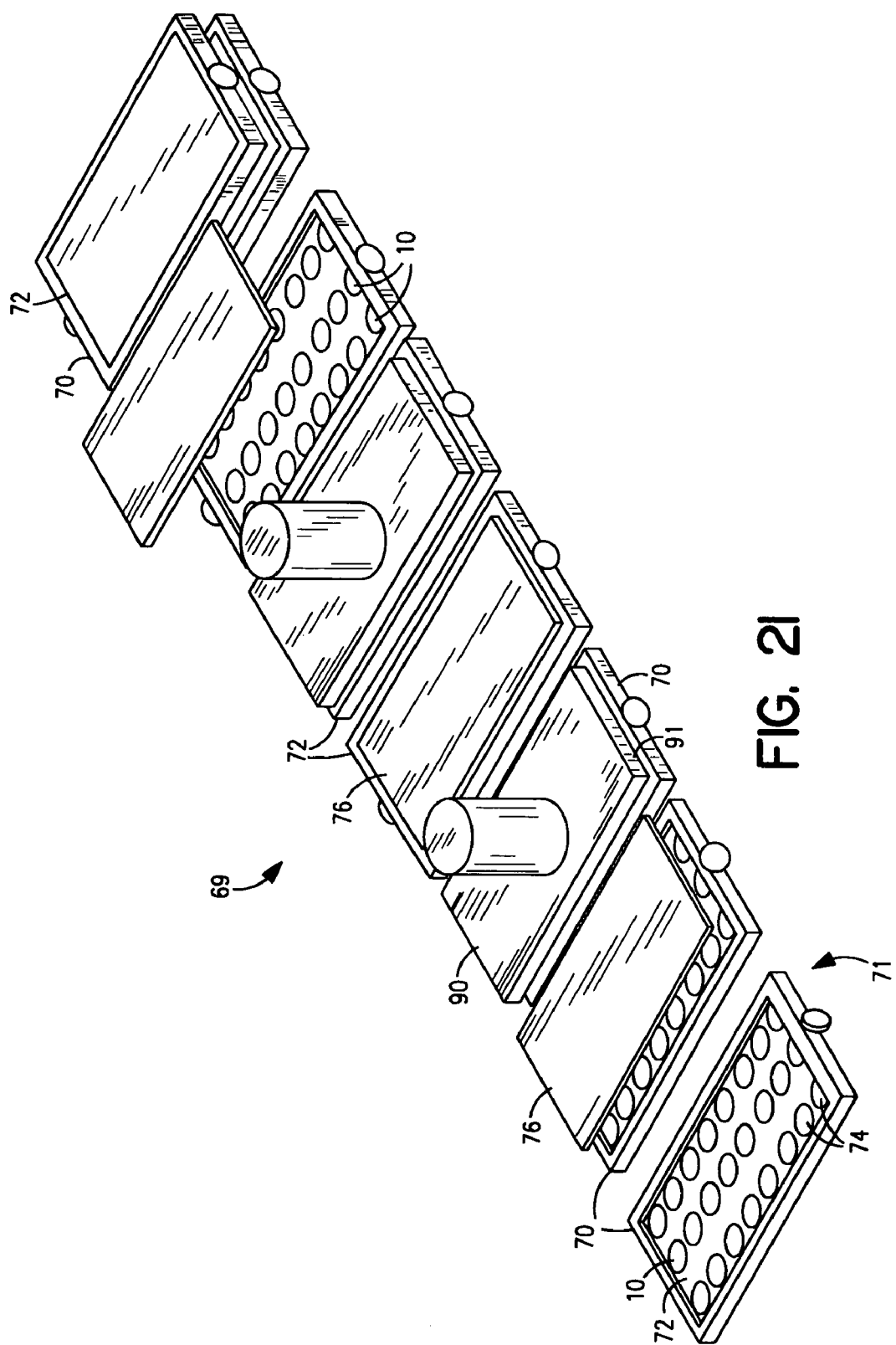
FIG. 21 is a simplified view in perspective of a linear frame-and-transfer plate type of apparatus for manufacturing holographic pharmaceuticals according to the present invention.
Figure 22:
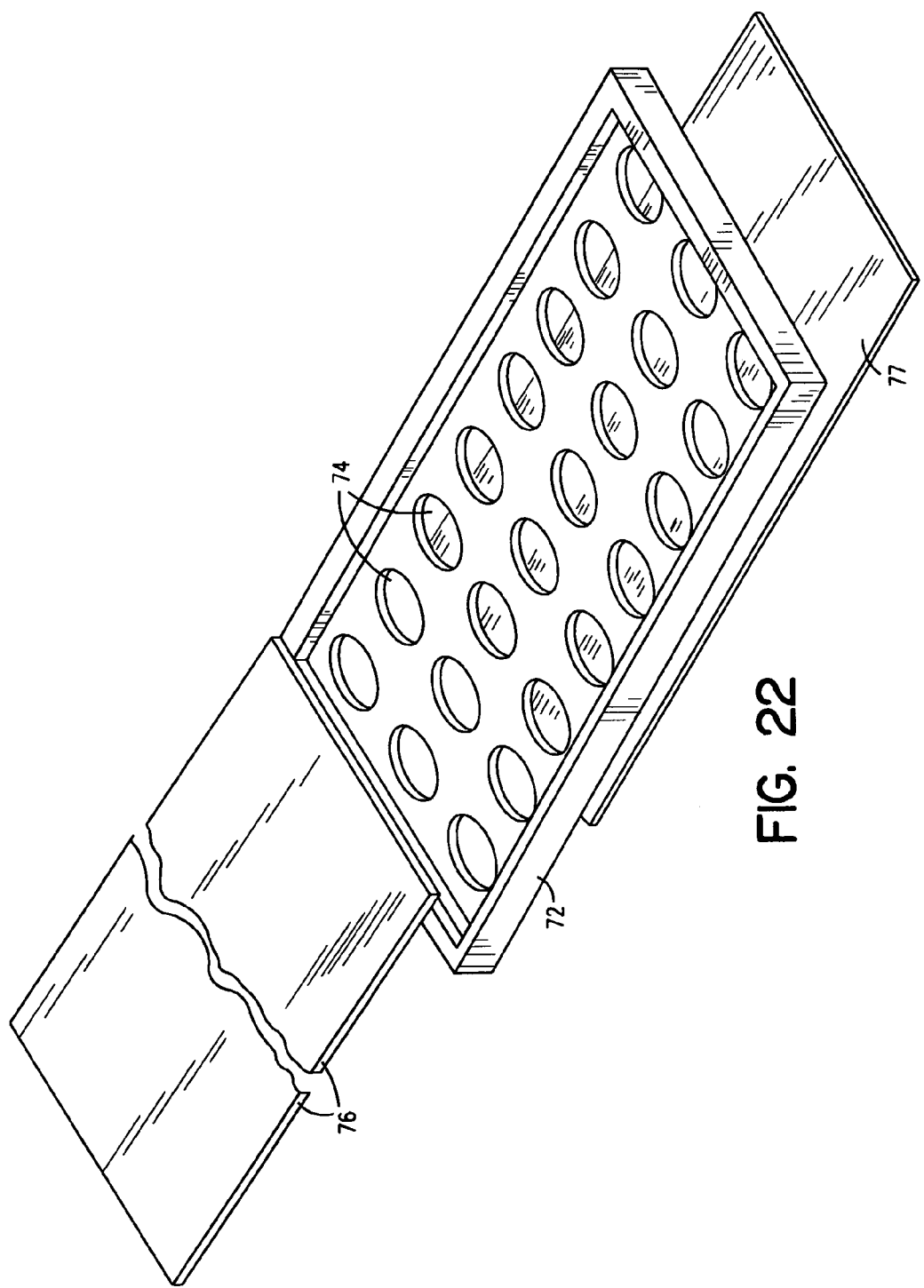
FIG. 22 is a detailed view in perspective of the frame-and-transfer-plate unit shown in FIG. 21.
Figure 23:
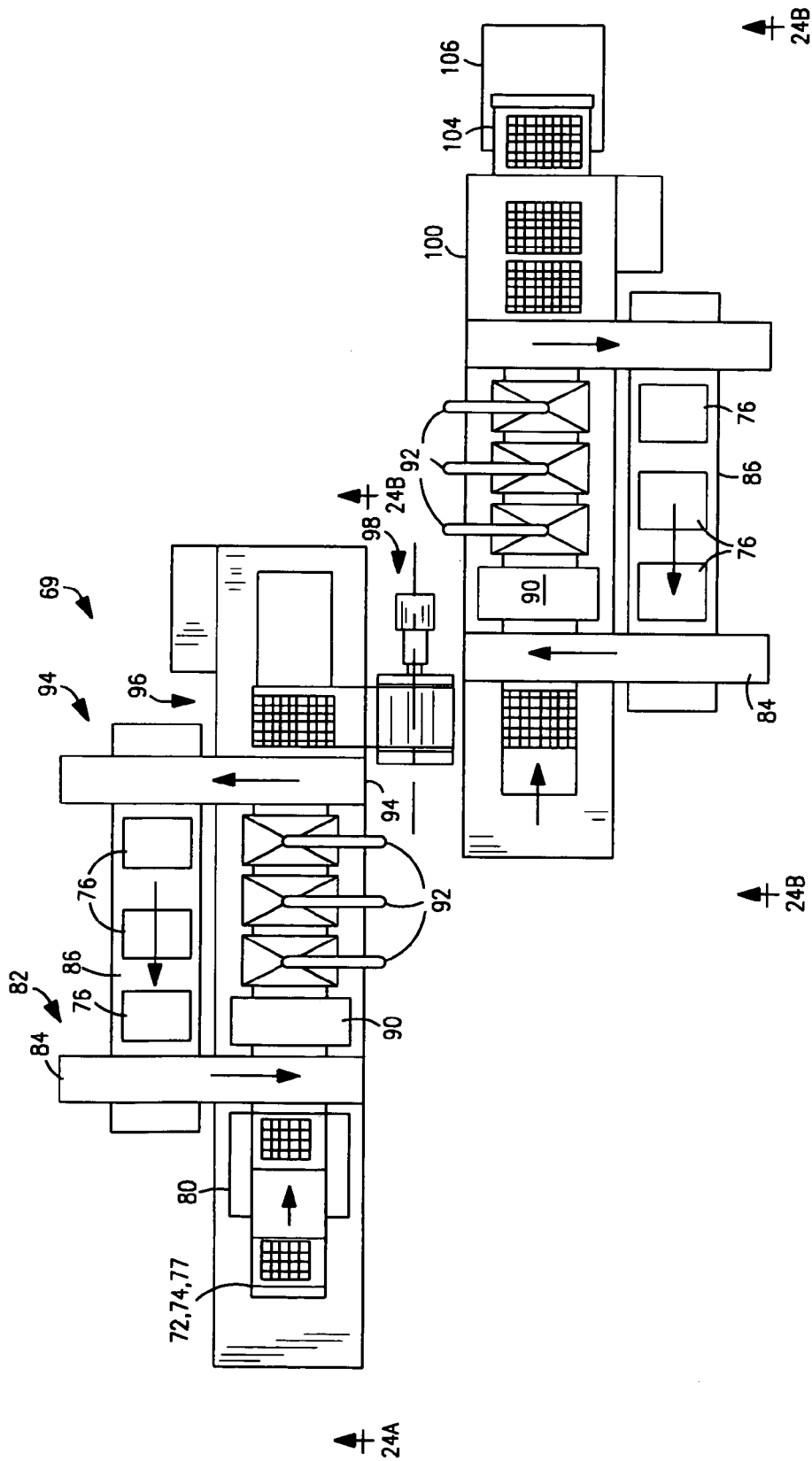
FIG. 23 is a top plan view of an apparatus using the constructions and a method of operation according to FIGS. 20 and 21.
Figure 24A:
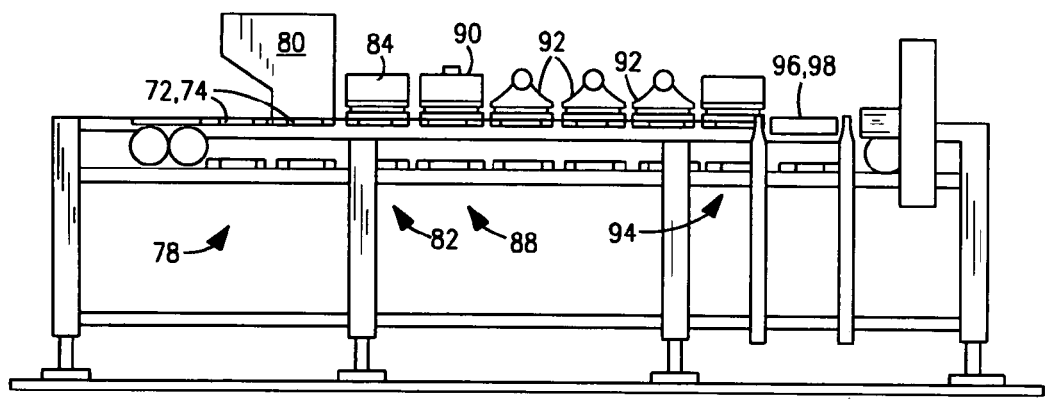
FIGS. 24A and 24B are views in side elevation of the apparatus shown in FIG. 23 taken along the lines 24A—24A and 24B—24B, respectively.
Figure 24B:
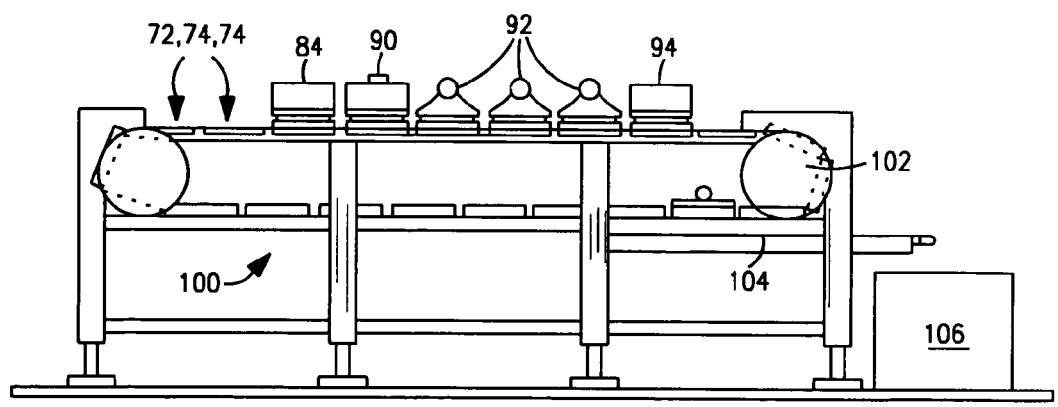

The frames are carried on a continuous conveyor belt, as best seen in FIG. 23, in two stages that each transfer a microrelief pattern 16 onto one face 18 of each dosage form 10. At a second station 82, pick-and-place mechanism 84 transfers plate 76 on a parallel transfer plate-return conveyor 86 and move it onto a frame 70, over an array of the dosage forms 10 loaded into the grid 72. At station 88 a thermal-pressure element 90 lowers onto the transfer plate, heats at least the portions of the coatings 12 adjacent the transfer plate to the desired temperature (90° C.–150° C., and preferably about 125° C.), and presses the transfer plate into the heated coating 12 to replicate the microrelief pattern. This typically requires about ½ second, but can fall in the range of 0.3 to 3.0 second. The thermal transfer element, as seen in FIG. 21, preferably has a heated pressure plate 91 that is generally co-extensive with the transfer plate to heat it and apply pressure to it uniformly. As noted above, a resilient layer, here the foam rubber base 77, helps to promote an even distribution of the applied force. A typical pressure is 5 kg to 30 kg/per pill with about 10 kg/per pill being preferred. After imprinting, the heat transfer element 90 moves and lifts from the transfer plate and the pallet 71 moves through several air cooling stations 92 (e.g., regions under cooled air outlets 93) which set the microrelief. At station 94, the transfer plate is then lifted from the pallet 71 to de-mold it from the dosage forms 10, and transfer it to the conveyor 86 for recirculation back to station 82.

A turnover mechanism 98 flips the dosage form array sandwiched between the two frame assemblies through 180° onto a second linear conveyor 100 of the second stage. This second stage repeats the microrelief replication process of stage one to place a microrelief on the opposite face 18 each dosage form 10. After the transfer plate 32 is removed at station 94, the registration grid and frame are carried around roll 102 to discharge the dosage forms to a take-away conveyor 104 feeding a collection bin 106.

Figure 25:
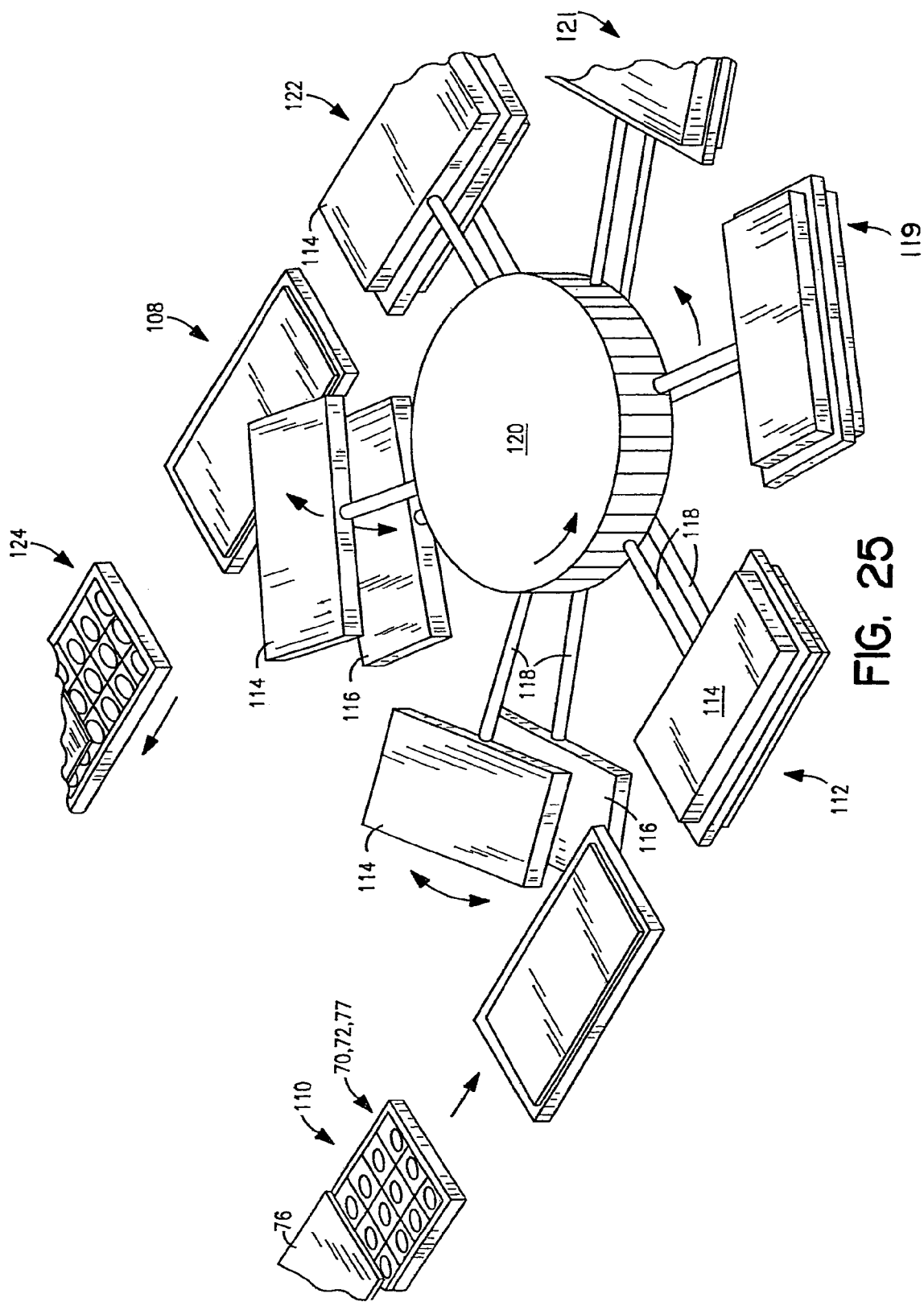
FIG. 25 is a view in perspective of an alternative embodiment of a rotary apparatus according to the present invention operating on frame-and-transfer-plate units of the type shown in FIG. 22.

FIG. 25 shows a rotary apparatus 108 for thermoforming a high resolution diffraction relief onto a layer 12 on an array of dosage forms 10 carried in a pallet 71. A diffraction pattern transfer plate 76 is placed on each incoming pallet 71 at 110. The pallet is then transported to a position 112 where it is gripped between a pair of members 114, 116 each supported on the end of an arm 118 rotated by a hub 120. At least one arm 118 of each pair of pivots to open, close, and press the transfer plate towards the dosage forms. As the hub rotates, a gripped assembly is heated and pressed at angular position 119, cooled at position 121, and released by opening the members 114, 116 at position 122 where the assembly is transported to a de-molding and transfer plate removal station 124.

Figure 26:
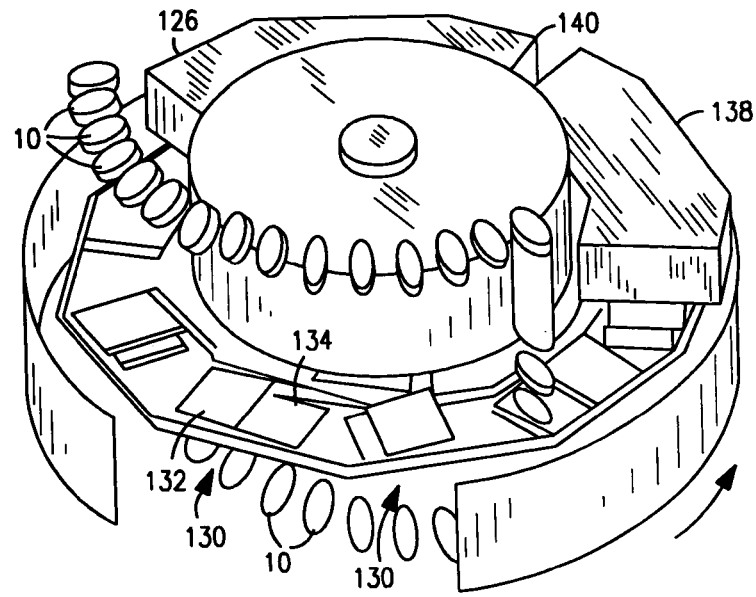
FIG. 26 is a view in perspective of an alternative rotary frame-and-transfer-plate-type apparatus according to the present invention.
Figure 27:
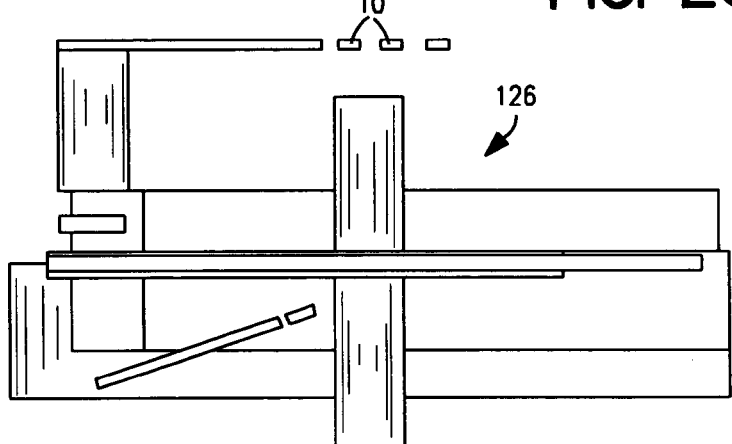
FIG. 27 is a view in side elevation of the apparatus shown in FIG. 26.
Figure 28:
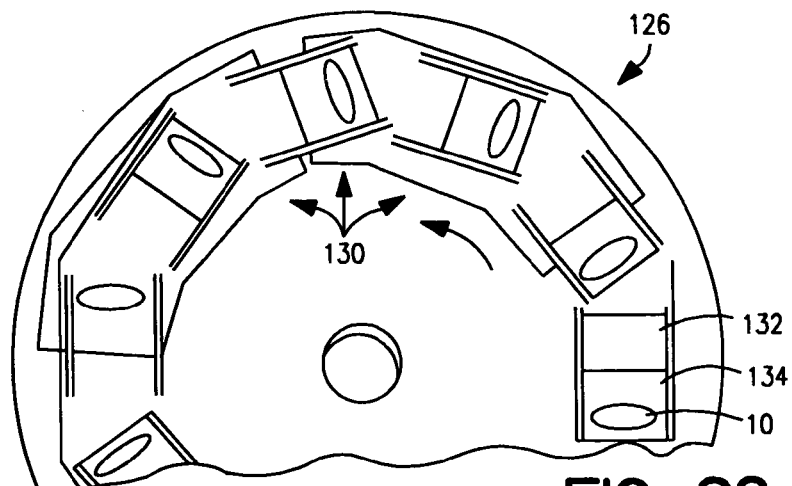
FIG. 28 is a detailed view in perspective of the replication assembly shown in FIGS. 26 and 27.

FIGS. 26 and 27 show a rotary apparatus 126 according to the present invention that receives an intake of dosage forms 10 that are fed vertically into a registration frame 128. An associated shuttle apparatus 130 moves both upper microstructure (relief) transfer element ("MTE") 132 and lower MTE plate 134 into and out of positions aligned with the frame 128. At the intake position 126, the upper MTE 132 is "open", that is, shuttled to the side, while the lower MTE 134 is "closed", that is, in position under the frame 128 to support the dosage form 10 in opening 136 in the MTE 128. The upper MTE then closes—as the apparatus rotates the dosage form(s) and MTE's through thermoforming and cooling positions 138 and 140, respectively. At position 142, the lower MTE 134 shuttles to an open position to allow the dosage forms to fall out of the frame 128 onto a chute, belt or other off-take arrangement.

It will be understood that the shuttle mechanism can include cam action or other equivalent mechanical arrangement to develop force that presses the MTE's toward the heated dosage form layers 12, and/or facilitates the release of the dosage forms from the MTE's. Also, pressing can utilize a separate pressure and/or heat applying member operating in the manner of the thermal transfer element 90.

Figure 29:
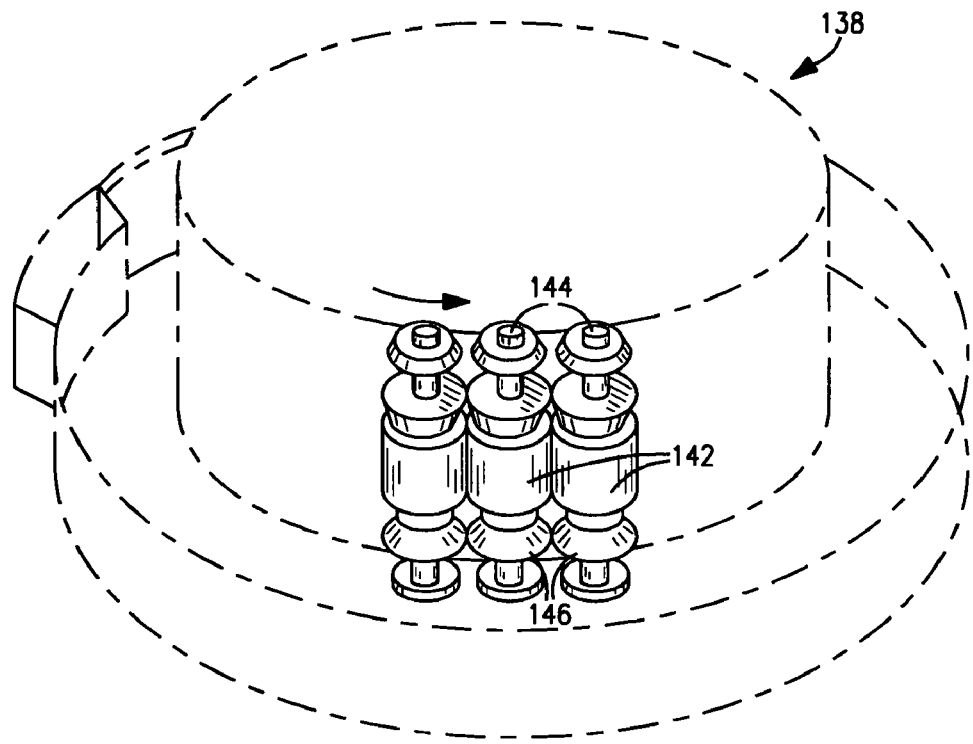
FIG. 29 is a view in perspective of a rotary die punch apparatus according to the present invention.
Figure 30:
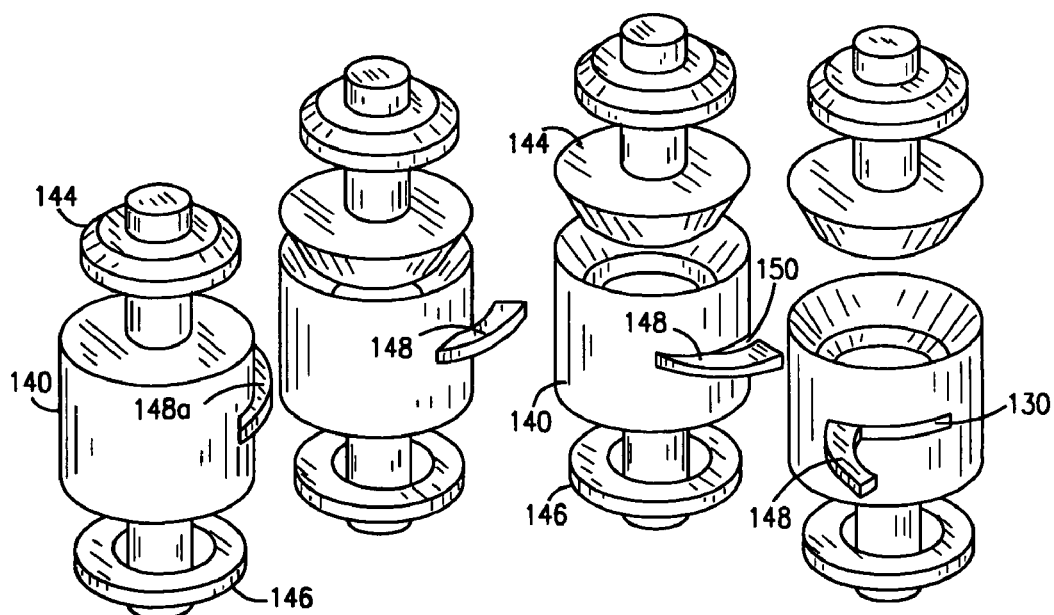
FIG. 30 is a detailed view in perspective of several die punches shown in FIG. 29 with a pivoted central tab operable to eject a tablet.

FIGS. 29 and 30 show another apparatus 138 according to the present invention that rotates a set of tablet punch dies 140 each having a body 142 with a central bore that defines the outline of this dosage form and upper and lower punches 144, 146 mounted for a coordinated, reciprocating, co-axial movement in opposite ends of the body 142. The punch dies are generally of standard design for the manufacture of compressed powder tablets, except that (1) the end face of each punch 144, 146 can carry a replaceable die with a high resolution microrelief pattern formed therein, and (2) a crescent-shaped tab 148 is mounted in a slot 150 in the side of the body 142 to execute a pivotal movement between the dosage form-in-die position 148a, shown at the left-most die in FIG. 30, and the dosage form-ejected-from-die position 148b, shown in the right-most die in FIG. 30. Alternatively, a small, movable clamp (not shown) can grip and move the dosage into, and hold them in position in, the dies 14, and then remove them from the dies 14.

In the apparatus 138 the dosage form 10 itself, not the punch or the die, is heated to soften the layer 12 before it is introduced to the apparatus 138. The heated dosage form is then fed into the die through the slot 150 with the tab in position 148b. Movement of the dosage form fully into the die is effected by rotating the tab 148 to position 148a. The apparatus then rotates to index the die, with the hot dosage form loaded therein, to a position where the cold punches 144, 146 are driven axially to transfer the microrelief pattern to the layer 12. Because the punches are relatively cold and have a large mass as compared to the heated dosage form, they quickly cool the layer 12. The punches are then withdrawn to de-mold the microrelief thus formed. Further step-wise rotation of the apparatus 138 brings the coated dosage form 10 with the microrelief(s) 16 to a discharge position. Operation of the tab 148 to the position 148b ejects the dosage form 10 from the die. The die punch is then ready to receive another heated dosage form. Alternatively, of course, the punches 144, 146 can be heated, and the dosage forms introduced at room temperature.

Figure 31:
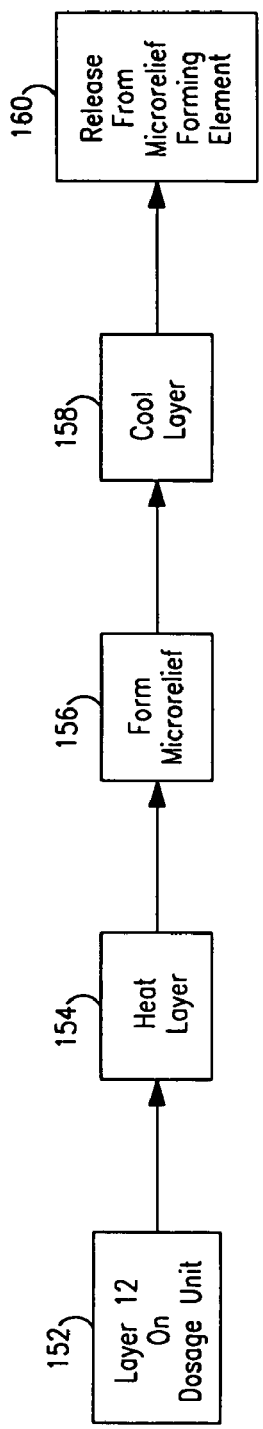
FIG. 31 is a flow diagram showing a highly generalized process according to the present invention for thermal forming a microrelief pattern on a solid, coated dosage form.

FIG. 31 is a flow diagram showing the thermoforming manufacturing process of the present invention in its most general form. At block 152 a layer 12 is solid state is provided, whether as a full or partial covering of a core 14, a hard or soft capsule shell, a label to be affixed to a core or capsule, or itself as a carrier of a pharmaceutical dispersed therein. At block 154 the layer is heated, whether by a mold or die or directly, to a degree sufficient to receive the microrelief. At block 156, the microrelief pattern is transferred into the heated layer. At block 158, the microrelief thus formed in the layer 12 is cooled to set the microrelief sufficiently that it does not degrade when de-molded. At block 160 the layer 12 is released from the mold (transfer plate, MTE, etc.).

Figure 32:
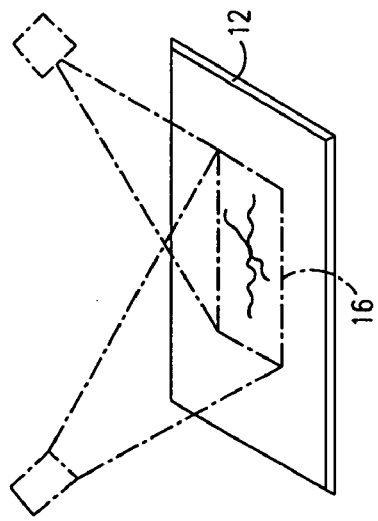
FIG. 32 is a schematic view in perspective of an apparatus according to the present invention for direct laser imprinting a diffraction relief pattern in an outer coating layer of a dosage form.

FIG. 32 shows an alternative arrangement for the formation of a holographic microrelief pattern directly into an outer layer 12 on a dosage form 10. A high energy laser light source 161 (shown as two sources 161, but typically it is one source whose output beam is split) produces two beams 162, 162 of laser light that interfere in a region 164 to produce a desired interference pattern 16 of light intensity maxima and minima. A dosage form is positioned with its layer 12 in the region 164. Lines of maximum light energy creates corresponding grooves (a microrelief) into the layer 12. Lines of minimum light intensity produce corresponding ridges in the layer 12. A microrelief pattern is thus formed directly by a pattern of light energy "burned into" the layer 12. Note that because the interference pattern occurs over a region, it automatically adjusts to variations of the layer 12 from a perfectly flat condition.

Figure 33:
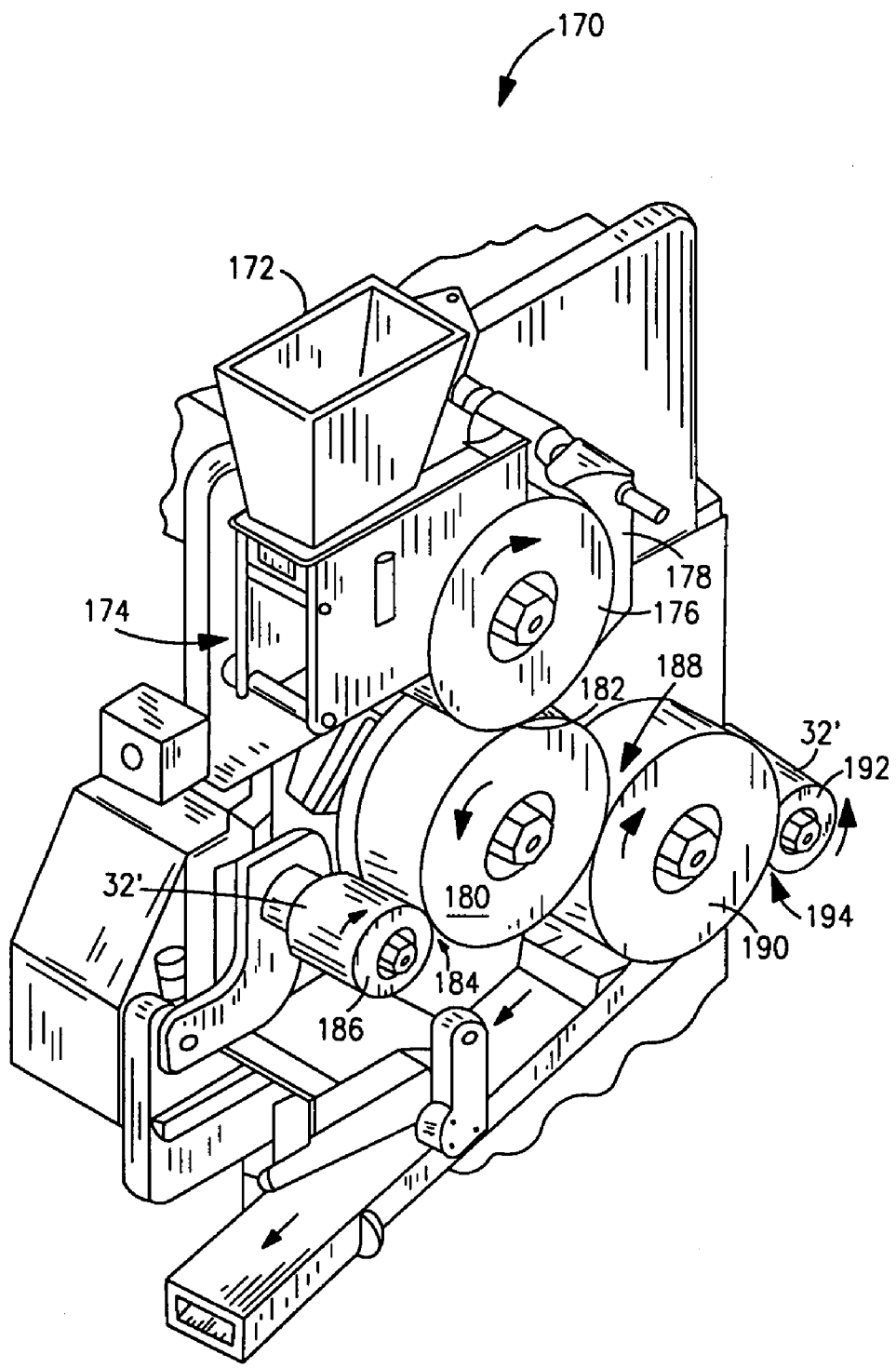
FIG. 33 is a view in perspective of an alternative apparatus according to the present invention that operates in the style of a high speed printer.

FIG. 33 shows a further alternative apparatus 170 according to the present invention that transfers a high resolution microrelief into the outer coating 12 of dosage forms 10, particularly tablets. This embodiment is similar in its construction and mode of operation to known high speed printing apparatuses. The dosage forms 10 are fed to an intake hopper 172. A feeding apparatus 174 takes the dosage forms from the hopper 172, orients and aligns them, and presents them for transfer to a first conveyor wheel 176. An array of depressions in the outer layer of the wheel 176, or other known arrangements, carry an array of the dosage forms on the outer periphery of the wheel 176. A guard rail 178 holds the dosage forms 10 in place on the conveyor 176 as it rotates them from the feeder 174 to a second conveyor wheel 180. The rotation of the conveyors 176 and 180 are coordinated so that the dosage forms transfer from the outer surface of the conveyor 176 to that of the conveyor 180 at the nip 182.

The conveyor wheel 180 then rotates the dosage forms to a nip 184 where a heated cylinder 186 that carries a microrelief transfer plate 32' on its outer surface. A microrelief pattern, preferably a high resolution diffraction relief, is electroformed or otherwise created using known techniques on the outer surface of the plate 32' and positioned to contact the layers 12 on a first face of the dosage forms 10 as they pass through the nip 184. The heat of the cylinder 186 softens the layer 12 to replicate the microrelief pattern in it. The size of the nip spacing, in conjunction with particular dosage forms, transfer plates and carrier wheel constructions (e.g., with or without a resilient backing layer under the dosage forms like layer 77 in the FIGS. 21–24 embodiment) produces the desired degree of pressure to affect the replication for a given layer 12 and a given degree of heating. Also, with the foregoing embodiments, a pressure in the range of 5 to 15 kg/pill, and preferably about 10 kg/pill, is preferred. A guard rail (not shown) like rail 178 may be used over the run to the nip 184, and in conjunction with other conveyor wheels runs, e.g., to hold the dosage forms on the wheel 180 after they leave the nip 184 and continue to nip 188 where the dosage forms again transfer to conveyor wheel 190.

Conveyor wheel 190, constructed like conveyor wheels 176 and 180, receives the array of dosage forms each having a microrelief in their outer layer 12 and carries them to a second heated cylinder 192 that rotates in registration with the wheel 190 to replicate a microrelief on a second face of the dosage forms in the manner described above with respect to heated cylinder 186 at nip 194. After replication of the microrelief at the nips 184 and 194, the layer 12 is cooled in any of the ways discussed above to retain the microrelief in the layer 12 and facilitate a demolding from the transfer plates 32',32'.

Having been embossed with a microrelief 16 on two opposite faces, the dosage forms 10 leaving the nip 194 are carried on the conveyor wheel 190 to an output chute 196 where the demolder dosage forms fall off the wheel 190 assisted by the force of gravity and slide down the chute 196.

There has been described a dosage form that can selectively retain and reconstruct optical information and effects while being compatible with modern high-speed production techniques. The dosage form can take a variety of configurations, including a coated tablet, a capsule, and If the layers themselves are formed into sections, they can be used as dosage forms after being made to absorb the contents of the pharmaceutically active agent of the core therein. The holographic images or effects can provide brand identification, control counterfeiting, and provide quality control. The dosage forms can be made using materials that have regulatory approval for foods or pharmaceutical uses.

There has also been described a variety of machines and processes for the production of these dosage forms. These machines and processes are compatible with modern production speeds and techniques. In the manufacture of dosage unit forms such as tablets, they also resist twinning.

While this invention has been described with respect to its presently preferred embodiments, other modifications and variations will occur to those skilled in this art. For example, those skilled in the art will readily understand that the products, apparatus, and manufacturing processes described herein can also be adapted to the production of non-pharmaceutical cores such as placebos and include cores made of materials such as sugar, gum, hard jellies, or a variety of confections. Such modifications and variations are intended to fall within the scope of the appended claims.

What is claimed is:

1. A method of producing a microrelief on an ingestible dosage form having a core which can contain a pharmaceutically active substance and a pharmaceutically acceptable carrier, comprising the steps of:
   a. coating said core with a layer of a thermo-formable material that can receive and retain a holographic diffraction pattern;
   b. providing a plate having a holographic diffraction pattern formed on at least a portion of a first surface thereof;
   c. transporting said coated cores to a position opposite said first surface;
   d. heating at least one of said plate and said coating during or prior to the time when they are in said opposed relationship;
   e. pressing said first surface into said coating to replicate said holographic diffraction pattern in said coating;
   f. cooling said coating thus replicated; and
   g. demolding said first plate surface from said coating wherein said heating raises the temperature of said diffraction pattern to a temperature in the range of 90–150° C., and wherein said pressing occurs for about 0.3 to 3.0 second.

2. The holographic dosage form production method of claim 1 wherein said coating is pan coating and further comprising the step of controlling twinning of said coated cores.

3. The holographic dosage form production method of claim 2 wherein said twinning control comprises forming said core with at least one curved face that receives said coating and said pressing.

4. The holographic dosage form production method of claim 3 wherein said curvature is sufficient to resist twinning, but not sufficient to distort the holographic image pressed into in said coating.

5. The holographic dosage form production method of claim 4 wherein said core face is generally circular and, measured as an angle in a plane through the face, the curvature is in the range of about 0.6 radian to about 0.9 radian.

6. The holographic dosage form production method of claim 2 wherein said twinning control comprises forming said core with a recess within at least one face of said coat, said recess having a generally flat bottom that receives said coating layer.

7. The holographic dosage form production method of claim 6 wherein said recess is sufficiently shallow that said pressing transfers said holographic pattern reliably.

8. The holographic dosage form production method of claim 7 wherein said recess is less than about 0.01 mm.

9. The holographic dosage form production method of claim 1 wherein said coating includes said thermo-formable material bonding reliably with said core.

10. The holographic dosage form production method of claim 1 or 9 wherein said thermo-formable material is selected from the group consisting of: gelatin, hydroxypropylmethylcellulose (HPMC), hydroxyproplycellulose (HPC), modified food starches, waxes, vegetable gums and combinations thereof.

11. The holographic dosage form production methods of claim 10 wherein said material includes solids of a modified cellulose, a plasticizer, and a colorant.

12. The holographic dosage form production method of claim 10 wherein said coating produces a layer in the range of 0.25% to 7.25% of the weight of said dosage form.

13. The holographic dosage form production method of claim 1 wherein said plate providing comprises continuously advancing a belt of a semi-flexible material containing said pattern on at least one surface thereof in coordinating with said transporting of said coated dosage forms.

14. The holographic dosage form production method of claim 13 wherein said semi-flexible material is selected from the group consisting of: a thin sheet metal, rubber, a laminate of thin sheet metal and a layer of a resilient backing material opposite said first surface, and a rubber and metal composite.

15. The holographic dosage form production method of claim 14 wherein said thin sheet metal is a nickel composite with a thickness of 1 mils to 5 mils, and said holographic diffraction pattern is electroformed on said first surface.

16. The holographic dosage form production method of claims 1 or 13 wherein said transporting also aligns said coated cores.

17. The holographic dosage form production method of claim 13 or 15 wherein said coated core facing said plate during said pressing is non-planar, and said belt flexibility is sufficient to allow said belt to conform to said non-planar coating desiring said pressing.

18. The holographic dosage form production method of claim 13 wherein said transporting comprises conveying of a linear array of said coated cores in a parallel, closely spaced relationship with a portion of said belt, and moving said belt in coordination with said conveying.

19. The holographic dosage form production method of claim 18 wherein said heating is a rapid, localized heating of said belt during said pressing.

20. The holographic dosage form production method of claim 19 wherein said pressing comprises a brief deflection of said heated belt that places said diffraction pattern in said coating to create said replication of said diffraction pattern in said coating.

21. The holographic dosage form production method of claim 18 wherein said cooling is a rapid, localized cooling that begins immediately after said pressing has formed said diffraction pattern in said coating.

22. The holographic dosage form production method of claim 21 wherein said demolding comprises a resumption of said mutually spaced relationship between said coating as said coated and said belt as they continue to move in coordination, after said cooling has begun.

\* \* \* \* \*